US010441716B2

(12) United States Patent
Schriver et al.

(10) Patent No.: US 10,441,716 B2
(45) Date of Patent: *Oct. 15, 2019

(54) FLUID MIXING CONTROL DEVICE FOR A MULTI-FLUID DELIVERY SYSTEM

(71) Applicant: BAYER HEALTHCARE LLC, Whippany, NJ (US)

(72) Inventors: Ralph H. Schriver, Tarentum, PA (US); Thomas P. Joyce, Wilkins Township, PA (US); Michael Riley, Saxonburg, PA (US); William D. Barlow, Beaver Falls, PA (US)

(73) Assignee: BAYER HEALTHCARE LLC, Whippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/864,448

(22) Filed: Jan. 8, 2018

(65) Prior Publication Data

US 2018/0147344 A1 May 31, 2018

Related U.S. Application Data

(63) Continuation of application No. 14/687,297, filed on Apr. 15, 2015, now Pat. No. 9,861,742, which is a (Continued)

(51) Int. Cl.
*A61M 5/168* (2006.01)
*G05D 11/00* (2006.01)
(Continued)

(52) U.S. Cl.
CPC ........ *A61M 5/16827* (2013.01); *A61M 5/007* (2013.01); *A61M 5/1407* (2013.01);
(Continued)

(58) Field of Classification Search
CPC .. A61M 5/007; A61M 5/1407; A61M 5/1409; A61M 5/31546; A61M 5/31548;
(Continued)

(56) References Cited

U.S. PATENT DOCUMENTS

| 281,734 A | 7/1883 | Smith |
| 377,907 A | 2/1888 | Pell |

(Continued)

FOREIGN PATENT DOCUMENTS

| CA | 2045070 A1 | 2/1992 |
| EP | 1172124 A2 | 1/2002 |

(Continued)

OTHER PUBLICATIONS

International Search Report and Written Opinion, dated Dec. 19, 2008, International Preliminary Report on Patentability from corresponding PCT Application No. PCT/US2008/80885, dated May 4, 2010.

(Continued)

*Primary Examiner* — Bhisma Mehta
*Assistant Examiner* — James D Ponton
(74) *Attorney, Agent, or Firm* — David Schramm; Joseph L. Kent; James R. Stevenson

(57) ABSTRACT

The control device is used to control delivery of fluids from a multi-fluid delivery system during a medical injection procedure. The fluid delivery system includes an injector used to deliver injection fluids to a patient. The control device is operatively associated with the injector for controlling discrete flow rates of injection fluids delivered to the patient. The control device includes first and second actuators associated with the manual control device, and an electronic substrate disposed within the manual control device and having a conductive pattern. The first actuator is operatively associated with the conductive pattern. The (Continued)

conductive pattern includes a plurality of predetermined digital values corresponding to discrete flow rates of injection fluids to be delivered by the injector. The second actuator is operatively associated with the electronic substrate and initiates output signals to the injector corresponding to desired mixture ratios of the injection fluids to be delivered by the injector.

20 Claims, 22 Drawing Sheets

Related U.S. Application Data continuation of application No. 12/265,060, filed on Nov. 5, 2008, now Pat. No. 9,011,377.

(51) Int. Cl.
| | | |
|---|---|---|
| G05D 11/02 | (2006.01) | |
| A61M 5/14 | (2006.01) | |
| G05D 7/06 | (2006.01) | |
| A61M 5/00 | (2006.01) | |
| A61M 5/315 | (2006.01) | |
| A61B 6/00 | (2006.01) | |
| A61M 5/178 | (2006.01) | |

(52) U.S. Cl.
CPC .... *A61M 5/16877* (2013.01); *A61M 5/31546* (2013.01); *A61M 5/31548* (2013.01); *G05D 7/0676* (2013.01); *G05D 11/003* (2013.01); *G05D 11/005* (2013.01); *G05D 11/02* (2013.01); *A61B 6/481* (2013.01); *A61M 2005/1787* (2013.01); *A61M 2205/18* (2013.01); *A61M 2205/50* (2013.01); *A61M 2205/502* (2013.01)

(58) Field of Classification Search
CPC .......... A61M 5/16827; A61M 5/16836; A61M 5/16877; A61M 5/19; A61M 5/2448; A61M 5/284; A61M 2005/14208; G05D 7/06; G05D 7/0617; G05D 7/0641; G05D 7/0647; G05D 7/0652; G05D 7/0658; G05D 7/0676; G05D 11/00; G05D 11/001; G05D 11/003; G05D 11/005; G05D 11/02; G05D 11/03; G05D 11/035; G05D 11/13; G05D 11/131
See application file for complete search history.

(56) References Cited

U.S. PATENT DOCUMENTS

| | | | |
|---|---|---|---|
| 1,675,718 A | 7/1928 | Lynch | |
| 1,748,810 A | 2/1930 | Wandel | |
| 1,844,380 A | 2/1932 | Cohen | |
| 2,062,285 A | 12/1936 | Bergman | |
| 2,335,085 A | 11/1943 | Roberts | |
| 2,485,842 A | 10/1949 | Pennington | |
| 2,590,838 A | 4/1952 | Boggs | |
| 2,702,547 A | 2/1955 | Glass | |
| 2,893,675 A | 7/1959 | Smith et al. | |
| 2,926,879 A | 3/1960 | Dietrich | |
| 2,985,192 A | 5/1961 | Taylor et al. | |
| 3,057,350 A | 10/1962 | Cowley | |
| 3,157,201 A | 11/1964 | Littmann | |
| 3,411,534 A | 11/1968 | Rose | |
| 3,450,152 A | 6/1969 | Phillip | |
| 3,464,359 A | 9/1969 | Charles et al. | |
| 3,701,345 A | 10/1972 | Heilman | |
| 3,834,372 A | 9/1974 | Turney | |
| 3,865,134 A | 2/1975 | Holcomb | |
| 3,918,490 A | 11/1975 | Goda | |
| 3,935,971 A | 2/1976 | Papoff et al. | |
| 3,957,082 A | 5/1976 | Fuson et al. | |
| 4,061,142 A | 12/1977 | Tuttle | |
| 4,071,039 A | 1/1978 | Goof | |
| 4,080,967 A | 3/1978 | O'Leary | |
| 4,094,318 A | 6/1978 | Burke et al. | |
| 4,121,622 A | 10/1978 | Forberg | |
| 4,230,151 A | 10/1980 | Jonsson | |
| 4,243,031 A | 1/1981 | Genese | |
| 4,246,452 A | 1/1981 | Chandler | |
| 4,259,985 A | 4/1981 | Bergmann | |
| 4,328,834 A | 5/1982 | Oates, Sr. et al. | |
| 4,351,332 A | 9/1982 | Whitney et al. | |
| 4,370,982 A | 2/1983 | Reilly | |
| 4,396,385 A | 8/1983 | Kelly et al. | |
| 4,459,053 A | 7/1984 | Sado et al. | |
| 4,464,172 A | 8/1984 | Lichtenstein | |
| 4,468,914 A | 9/1984 | Pestes | |
| 4,469,121 A | 9/1984 | Moen | |
| 4,474,351 A | 10/1984 | Thalenfeld | |
| 4,484,599 A | 11/1984 | Hanover et al. | |
| 4,491,156 A | 1/1985 | Lee, II | |
| 4,559,036 A | 12/1985 | Wunsch | |
| 4,637,817 A | 1/1987 | Archibald et al. | |
| 4,677,980 A | 7/1987 | Reilly et al. | |
| 4,684,102 A | 8/1987 | Dykstra | |
| 4,697,780 A | 10/1987 | Wenkman et al. | |
| 4,710,166 A | 12/1987 | Thompson et al. | |
| 4,721,276 A | 1/1988 | Moss | |
| 4,809,940 A | 3/1989 | Trestyn | |
| 4,819,637 A | 4/1989 | Dormandy, Jr. et al. | |
| 4,821,996 A | 4/1989 | Bellotti et al. | |
| 4,838,856 A | 6/1989 | Mulreany et al. | |
| 4,854,324 A | 8/1989 | Hirschman et al. | |
| 4,858,127 A | 8/1989 | Kron et al. | |
| 4,925,444 A | 5/1990 | Orkin et al. | |
| 4,936,753 A | 6/1990 | Kozumplik, Jr. et al. | |
| 4,946,434 A | 8/1990 | Plaisted et al. | |
| 4,967,797 A | 11/1990 | Manska | |
| 4,993,546 A | 2/1991 | Southard | |
| 5,002,528 A | 3/1991 | Palestrant | |
| 5,007,904 A | 4/1991 | Densmore et al. | |
| 5,021,046 A | 6/1991 | Wallace | |
| 5,057,081 A | 10/1991 | Sunderland et al. | |
| 5,084,031 A | 1/1992 | Todd et al. | |
| 5,097,840 A | 3/1992 | Wallace et al. | |
| 5,100,380 A | 3/1992 | Epstein et al. | |
| 5,104,387 A | 4/1992 | Pokorney et al. | |
| 5,106,379 A | 4/1992 | Leap | |
| 5,113,906 A | 5/1992 | Hoegner | |
| 5,117,870 A | 6/1992 | Goodale et al. | |
| 5,135,026 A | 8/1992 | Manska | |
| 5,136,026 A | 8/1992 | Romisch et al. | |
| 5,143,257 A | 9/1992 | Austin et al. | |
| 5,152,776 A | 10/1992 | Pinchuk | |
| 5,190,071 A | 3/1993 | Sule | |
| 5,199,604 A | 4/1993 | Palmer et al. | |
| 5,205,322 A | 4/1993 | Merick et al. | |
| 5,207,642 A | 5/1993 | Orkin et al. | |
| 5,259,985 A | 11/1993 | Nakanishi et al. | |
| 5,273,537 A | 12/1993 | Haskvitz et al. | |
| 5,300,031 A | 4/1994 | Neer et al. | |
| 5,336,051 A | 8/1994 | Tamari | |
| 5,356,375 A | 10/1994 | Higley | |
| 5,377,718 A | 1/1995 | Sand | |
| 5,383,858 A | 1/1995 | Reilly et al. | |
| 5,429,611 A | 7/1995 | Rait | |
| 5,433,712 A | 7/1995 | Stiles et al. | |
| 5,450,847 A | 9/1995 | Kampfe et al. | |
| 5,460,609 A | 10/1995 | O'Donnell | |
| 5,462,251 A | 10/1995 | Kawabe | |
| 5,478,318 A | 12/1995 | Yoon | |
| 5,515,851 A | 5/1996 | Goldstein | |
| 5,529,463 A | 6/1996 | Layer et al. | |
| 5,562,614 A | 10/1996 | O'Donnell | |
| 5,569,208 A | 10/1996 | Woelpper et al. | |
| 5,573,505 A | 11/1996 | Johnson et al. | |
| 5,573,515 A | 11/1996 | Wilson et al. | |
| 5,584,671 A | 12/1996 | Schweitzer, Jr. et al. | |

(56) References Cited

U.S. PATENT DOCUMENTS

| | | |
|---|---|---|
| 5,592,940 A | 1/1997 | Kampfe et al. |
| 5,672,155 A | 9/1997 | Riley et al. |
| 5,730,418 A | 3/1998 | Feith et al. |
| 5,770,675 A | 6/1998 | Kim et al. |
| 5,779,675 A | 7/1998 | Reilly et al. |
| 5,800,397 A | 9/1998 | Wilson et al. |
| 5,806,519 A | 9/1998 | Evans, III et al. |
| 5,807,349 A | 9/1998 | Person et al. |
| 5,817,068 A | 10/1998 | Urrutia |
| 5,840,026 A | 11/1998 | Uber, III et al. |
| 5,842,671 A | 12/1998 | Gibbs |
| 5,865,797 A * | 2/1999 | Zeeman .............. A61M 5/1408 604/246 |
| 5,873,861 A | 2/1999 | Hitchins et al. |
| 5,882,343 A | 3/1999 | Wilson et al. |
| 5,885,216 A | 3/1999 | Evans, III et al. |
| 5,901,745 A | 5/1999 | Buchtel |
| 5,916,165 A | 6/1999 | Duchon et al. |
| 5,916,197 A | 6/1999 | Reilly et al. |
| 5,938,639 A | 8/1999 | Reilly et al. |
| 5,947,431 A | 9/1999 | Kiggins |
| 5,947,935 A | 9/1999 | Rhinehart et al. |
| 5,988,587 A | 11/1999 | Duchon et al. |
| 6,079,691 A | 6/2000 | Dragone |
| 6,096,011 A | 8/2000 | Trombley, III et al. |
| 6,099,502 A | 8/2000 | Duchon et al. |
| 6,197,000 B1 | 3/2001 | Reilly et al. |
| 6,221,045 B1 | 4/2001 | Duchon et al. |
| 6,293,958 B1 | 9/2001 | Berry et al. |
| 6,306,117 B1 | 10/2001 | Uber, III |
| 6,329,236 B1 | 12/2001 | Choi et al. |
| 6,336,913 B1 | 1/2002 | Spohn et al. |
| 6,339,718 B1 | 1/2002 | Zatezalo et al. |
| 6,344,030 B1 | 2/2002 | Duchon et al. |
| 6,361,528 B1 | 3/2002 | Wilson et al. |
| 6,436,072 B1 | 8/2002 | Kullas et al. |
| 6,442,418 B1 | 8/2002 | Evans, III et al. |
| 6,447,481 B1 | 9/2002 | Duchon et al. |
| 6,471,674 B1 | 10/2002 | Emig et al. |
| 6,475,192 B1 | 11/2002 | Reilly et al. |
| 6,488,660 B1 | 12/2002 | Futterknecht |
| RE38,074 E | 4/2003 | Recinella et al. |
| 6,557,738 B1 | 5/2003 | Meintzer |
| 6,558,125 B1 | 5/2003 | Futterknecht |
| 6,575,930 B1 | 6/2003 | Trombley, III et al. |
| 6,626,862 B1 | 9/2003 | Duchon et al. |
| 6,638,263 B1 | 10/2003 | Theeuwes et al. |
| 6,643,537 B1 | 11/2003 | Zatezalo et al. |
| 6,648,017 B2 | 11/2003 | Lamas et al. |
| 6,652,489 B2 | 11/2003 | Trocki et al. |
| 6,656,157 B1 | 12/2003 | Duchon et al. |
| 6,669,679 B1 | 12/2003 | Savage et al. |
| 6,676,104 B2 | 1/2004 | Tillander |
| 6,682,044 B2 | 1/2004 | Miller |
| 6,708,944 B2 | 3/2004 | Pfeil et al. |
| 6,731,971 B2 | 5/2004 | Evans et al. |
| 6,746,427 B2 | 6/2004 | Duchon et al. |
| 6,749,090 B2 | 6/2004 | Bailey |
| 6,752,789 B2 | 6/2004 | Duchon et al. |
| 6,857,617 B2 | 2/2005 | Forberg et al. |
| 6,866,039 B1 | 3/2005 | Wright et al. |
| 6,866,654 B2 | 3/2005 | Callan et al. |
| 6,871,660 B2 | 3/2005 | Hampsch |
| 6,880,808 B2 | 4/2005 | McPeak et al. |
| 6,889,074 B2 | 5/2005 | Uber et al. |
| 6,892,996 B2 | 5/2005 | Starchevich |
| 6,901,283 B2 | 5/2005 | Evans et al. |
| 6,918,893 B2 | 7/2005 | Houde et al. |
| 6,929,235 B1 | 8/2005 | Height et al. |
| 6,929,236 B1 | 8/2005 | Height et al. |
| 6,929,619 B2 | 8/2005 | Fago et al. |
| 6,945,959 B2 | 9/2005 | Duchon et al. |
| 6,953,450 B2 | 10/2005 | Baldwin et al. |
| 6,953,453 B2 | 10/2005 | Recinella et al. |
| 6,958,053 B1 | 10/2005 | Reilly |
| 7,018,363 B2 | 3/2006 | Cowan et al. |
| 7,047,058 B1 | 5/2006 | Dvorsky et al. |
| 7,060,049 B2 | 6/2006 | Trombley et al. |
| 7,094,216 B2 | 8/2006 | Trombley et al. |
| 7,153,288 B2 | 12/2006 | Duchon et al. |
| 7,192,416 B1 | 3/2007 | Lazzaro et al. |
| 7,267,667 B2 | 9/2007 | Houde et al. |
| 7,326,186 B2 | 2/2008 | Trombley et al. |
| 7,549,977 B2 | 6/2009 | Schriver et al. |
| 7,553,294 B2 | 6/2009 | Lazzaro et al. |
| 7,556,619 B2 | 7/2009 | Spohn et al. |
| 7,563,249 B2 | 7/2009 | Schriver et al. |
| 7,566,320 B2 | 7/2009 | Duchon et al. |
| 7,611,503 B2 | 11/2009 | Spohn et al. |
| 7,618,397 B2 | 11/2009 | Hicks |
| 7,662,124 B2 | 2/2010 | Duchon et al. |
| 7,666,169 B2 | 2/2010 | Cowan et al. |
| D618,334 S | 6/2010 | Le et al. |
| 7,766,883 B2 | 8/2010 | Rellly et al. |
| 7,879,008 B2 | 2/2011 | Haury et al. |
| 7,959,121 B1 | 6/2011 | Barnes, Jr. |
| 8,033,518 B2 | 10/2011 | Schuchman |
| 8,133,205 B2 | 3/2012 | Rhinehart et al. |
| 8,192,397 B2 | 6/2012 | Griffiths et al. |
| 8,596,601 B1 | 12/2013 | Andersen |
| 9,011,377 B2 * | 4/2015 | Schriver .............. A61M 5/1407 604/151 |
| 9,861,742 B2 * | 1/2018 | Schriver .............. A61M 5/1407 |
| 2002/0088954 A1 | 7/2002 | Miller |
| 2002/0130283 A1 | 9/2002 | Starchevich |
| 2002/0183616 A1 | 12/2002 | Toews et al. |
| 2003/0071233 A1 | 4/2003 | Stewart et al. |
| 2003/0079746 A1 | 5/2003 | Hickle |
| 2003/0139706 A1 | 7/2003 | Gray |
| 2004/0064041 A1 | 4/2004 | Lazzaro et al. |
| 2004/0092885 A1 | 5/2004 | Duchon et al. |
| 2004/0122370 A1 | 6/2004 | Joyce et al. |
| 2004/0158205 A1 | 8/2004 | Savage |
| 2004/0241023 A1 | 12/2004 | Pinkerton et al. |
| 2004/0254333 A1 | 12/2004 | Smits et al. |
| 2004/0254533 A1 | 12/2004 | Schriver et al. |
| 2005/0104444 A1 | 5/2005 | Callan et al. |
| 2005/0113754 A1 | 5/2005 | Cowan et al. |
| 2005/0230575 A1 | 10/2005 | Zelenski et al. |
| 2005/0234407 A1 | 10/2005 | Spohn et al. |
| 2005/0234428 A1 | 10/2005 | Spohn et al. |
| 2005/0245883 A1 | 11/2005 | Baldwin |
| 2005/0273056 A1 | 12/2005 | Haury et al. |
| 2006/0108008 A1 | 5/2006 | Guala |
| 2006/0155248 A1 | 7/2006 | Hashimoto et al. |
| 2006/0167415 A1 | 7/2006 | Nemoto |
| 2006/0178632 A1 | 8/2006 | Trombley, III |
| 2006/0184124 A1 | 8/2006 | Cowan et al. |
| 2007/0060874 A1 | 3/2007 | Nesbitt et al. |
| 2007/0204612 A1 | 9/2007 | Klimowicz et al. |
| 2007/0244437 A1 | 10/2007 | Castillo et al. |
| 2008/0058758 A1 | 3/2008 | Ranchod et al. |
| 2008/0086087 A1 | 4/2008 | Spohn et al. |
| 2008/0103437 A1 | 5/2008 | Duchon et al. |
| 2008/0269678 A1 | 10/2008 | Rebours |
| 2009/0112164 A1 | 4/2009 | Reilly et al. |
| 2010/0114040 A1 | 5/2010 | Schriver et al. |
| 2011/0002802 A1 | 1/2011 | Capone et al. |
| 2012/0244018 A1 | 9/2012 | Reilly |
| 2014/0224829 A1 | 8/2014 | Capone et al. |

FOREIGN PATENT DOCUMENTS

| | | |
|---|---|---|
| GB | 2108852 A | 5/1983 |
| JP | H06142199 A | 5/1994 |
| JP | H06142200 A | 5/1994 |
| WO | 9707841 A2 | 3/1997 |
| WO | 0010629 A1 | 3/2000 |
| WO | 0152921 A2 | 7/2001 |
| WO | 0204049 A1 | 1/2002 |
| WO | 03015851 A1 | 2/2003 |
| WO | 2006056828 A1 | 6/2006 |
| WO | 2012155035 A1 | 11/2012 |

(56) References Cited

FOREIGN PATENT DOCUMENTS

OTHER PUBLICATIONS

International Search Report in corresponding International Application PCT/US2008/080855 dated Dec. 19, 2008.

* cited by examiner

FLUID MIXING CONTROL DEVICE FOR A MULTI-FLUID DELIVERY SYSTEM

RELATED APPLICATIONS

The present application is a continuation application from U.S. patent application Ser. No. 14/687,297, filed Apr. 15, 2015, now U.S. Pat. No. 9,861,742, which is a continuation application from U.S. patent application Ser. No. 12/265,060, filed Nov. 5, 2008, now U.S. Pat. No. 9,011,377, the disclosures of which are incorporated by this reference. The present application incorporates by reference U.S. patent application Ser. No. 11/085,616, filed Mar. 21, 2005, now U.S. Pat. No. 7,879,008, and U.S. patent application Ser. No. 11/928,021, filed Oct. 30, 2007, now U.S. Pat. No. 7,766,883, the disclosures of which are incorporated herein by reference in their entirety

BACKGROUND

Field of the Disclosure

The present disclosure relates generally to control devices for controlling operation of fluid-supplying machines or apparatus used in medical procedures such as angiography and, further, to hand-held control devices for controlling the flow rate of fluids, such as contrast media and/or common flushing agents, injected into a patient during medical procedures, such as angiography.

Description of Related Art

Angiography is a procedure used in the detection and treatment of abnormalities or restrictions in blood vessels. During angiography, a radiographic image of a vascular structure (i.e., blood vessel) is obtained by injecting radiographic contrast material, also referred to as contrast media, through a catheter into a vein or artery. X-rays are passed through the region of the body in which the contrast media is concentrated. The X-rays are absorbed by the contrast material, causing a radiographic outline or image of the blood vessel containing the contrast media. The X-ray's images of the blood vessel filled with the contrast media are usually recorded onto film or videotape and are displayed on a fluoroscope monitor.

Many angiographic procedures, in particular coronary angiography and especially coronary vascular interventional procedures such as angioplasty, require frequent intermittent injections of contrast media. The contrast media is administered in varying volumes as well as modulated strengths and time durations. The intermittent contrast media injections are critical for optimal positioning of guiding catheters at the targeted blood vessels, positioning of guide wires to and through the targeted areas during catheter interventions (i.e., percutaneous transluminal coronary angioplasty), and for assessment of the results of such interventional procedures.

During angiography, after a physician places the angiographic catheter into a vein or artery, the angiographic catheter is connected to either a manual or an automatic contrast media injection mechanism. A typical manual contrast media injection mechanism includes a syringe and a catheter connection. The user of the manual contrast media injection mechanism adjusts the rate and volume of injection by altering the manual actuation force applied to the plunger of the syringe.

Automatic contrast media injection mechanisms typically involve a syringe connected to a linear actuator. The linear actuator is connected to a motor which is controlled electronically. The operator enters into the electronic control a fixed volume of contrast media and a fixed rate of injection. There is typically no interactive control between the operator and the mechanism, except to start or stop the injection. A change in flow rate occurs by stopping the mechanism and resetting the parameters.

Recent improvements in the radiographic imaging field have attempted to apply software and hardware interfaces to automatic contrast media injection mechanisms to provide variable flow rate and fixed flow rate modes to the operator. Additionally, the delivery of common flushing agents, such as saline, may also be controlled using the software/hardware interfaces. One such angiographic control device is disclosed in U.S. Pat. No. 5,515,851 to Goldstein. The Goldstein patent discloses the use of a microchip control device in the form of an angiographic control pad device designed to facilitate finger touch modulation of flow rate, volume, and duration of contrast media injection into a patient during an angiographic procedure. The control finger pad device allows the operator to control the aforementioned parameters during an injection procedure by altering the duration and extent of fingertip depression on the finger pads.

Another control device used to provide variable flow rate control to an operator of an automatic contrast media injection mechanism is disclosed in U.S. Pat. No. 5,916,165 to Duchon et al. This reference discloses a hand-held pneumatic control device that interfaces with and controls a fluid supply or injection mechanism. The hand-held control device is further adapted to control dispensement of saline injected into the patient during the angiographic procedure. The hand-held control device is generally adapted to be responsive to fluid pressure within the device. The control device includes a pressure control member adapted to selectively change fluid pressure within the pressure control member based on inputs from the operator. In one embodiment, the control device is provided with one or more internal air bladders having a volume that selectively adjusts to change the fluid pressure within the air bladders based on operator inputs. Internal sensors are provided to monitor the volume changes of the air bladders, and generate control signals based on the volume changes.

U.S. Pat. No. 5,988,587, also to Duchon et al., discloses another version of a hand-held control device for an automatic contrast media injection mechanism. This reference discloses a hand-held control device that includes two opposing and spaced-apart handles. A resilient attachment member connects the two handles. The resilient attachment member is configured to allow the first handle to move with respect to the second handle in response to operator inputs. The control device includes a sensor attached to the first handle for producing a variable control signal indicative of the distance between the first handle and the second handle.

Yet another hand-held control device is disclosed in U.S. Pat. No. 6,221,045 to Duchon et al. This reference discloses a hand-held control device that generates a control signal that is continuously variable according to continuously varying movement of a user's hand on the hand-held control. The control signal is continuously variable and sustainable at any value between preset maximum and minimum values corresponding to maximum and minimum contrast media discharge flow rates.

It is also known that the concept of diluting contrast with saline is gaining in popularity in the medical imaging industry. Certain solutions for automating this process already exist. However, some known "mixing" solutions are somewhat low tech. They often involve mixing by hand in either a sterile bowl or syringe. Prior art hand control devices in the market today do not provide such a mixing capability. Further, future generations of injector equipment that might permit mixing may be limited in that, once the injection is started, the mixture of contrast and saline cannot be adjusted.

As automatic contrast media/fluid injection mechanisms and systems become more complex, it is desirable to interface with such mechanisms and systems on a digital level to afford more control over the medical injection procedures performed with such devices. The foregoing examples of hand-held control devices provide a certain amount of control over such procedures by offering the operator of the contrast media/fluid injection mechanism or system a variable flow rate mode of operating the mechanism or system. However, there is room for improvement in the field of control devices for controlling or operating contrast media/fluid injection mechanisms or systems, for example, by providing a control device that may interface with such mechanisms or systems on a truly digital level, while providing accurate flow rate control of contrast media injection and/or saline flush control and, desirably, controlled mixing of contrast media and saline. Additionally, there is a need for a hand-held control device that is simple to use, for example, having an intuitive look and feel of operation for the operator. Further, a need exists for a hand-held control device that is simple and inexpensive to manufacture, so that the device itself may be disposable after a preset number of uses.

BRIEF SUMMARY

Generally, a fluid delivery system is disclosed herein for use in medical injection procedures that includes a control device for controlling flow rates of fluid delivered from the fluid delivery system to a patient. The fluid delivery system typically includes an injector, for example, a powered injector for delivering fluid to the patient. The control device is generally adapted to control flow rates of fluid delivered by the injector to the patient. In particular, the control device is adapted to provide a user of the control device with the ability to vary the flow rates of fluid from the injector.

The fluid delivery system and control device may be used in medical injection procedures, such as angiography. In such procedures, as indicated previously, an injector, either manual or powered, is used to deliver fluids, particularly contrast media, under pressure to a patient. Typically, the patient is connected to a syringe associated with the injector by a catheter. The contrast media is injected into the patient upon actuation of the injector. The disclosed control device is generally adapted to control the injection fluid flow rate to the patient from the injector, for example, a powered injector. Thus, the control device provides the operator of a powered injector with a variable flow rate mode to deliver contrast media at discrete flow rates desired by the operator, who is typically a medical practitioner.

Additionally, the control device is generally adapted to control the delivery of additional injection fluids beyond contrast media. For example, it is common to supply saline to the patient during certain aspects of injection procedures, such as angiography. The control device is further adapted to start and stop the flow of an additional fluid, such as saline, to the patient when commanded by the user. If desired, the control device may be adapted to allow mixing of contrast media with flushing media. Such mixing may be real-time and the device may allow both real-time variability of flow rate and variability of contrast media/saline mix (or of any two desired fluids). Such a mixing control device typically interfaces with a multi-axis or multi-fluid injection/delivery system which receives and acts upon signals outputted by the mixing control device.

Moreover, the control device may be configured to be hand-held and may be ergonomically designed to fit comfortably within the human hand. Further, the control device may be provided as a disposable device, typically used for only a certain number of procedures before being discarded.

A fluid delivery system according to one embodiment generally includes an injector that may be adapted to actuate a syringe used to deliver an injection fluid to a patient, and a control device operatively associated with the injector, either directly or indirectly, for controlling flow rates of the injection fluid delivered to the patient. The control device generally includes a housing and an actuator associated with the housing. The control device further includes an electronic substrate disposed within the housing. The electronic substrate comprises a conductive pattern, defined or formed thereon. The actuator is adapted for operative association with the conductive pattern when actuated by a user. The conductive pattern may comprise a plurality of predetermined digital values corresponding to discrete flow rates of injection fluid to be delivered by the injector, such that when the actuator is actuated, the actuator operatively associates with the conductive pattern and transmits the digital values to the injector.

The actuator may be movably associated with the housing for operatively associating with the conductive pattern. The digital values may be arranged such that the discrete flow rates are linearly proportional to distance of movement of the actuator. Additionally, the digital values may be arranged such that the discrete flow rates incrementally increase with distance of movement of the actuator. The incremental increase may comprise 5%, 10%, 20%, or any desired incremental increase with each digital value. The digital values typically include at least a first digital value corresponding to no movement of the actuator and a 0% (i.e., no) discrete flow rate, and a last digital value corresponding to a maximum movement of the actuator and a 100% (i.e., full) discrete flow rate. The last digital value may correspond to a maximum possible flow rate from the injector.

The actuator may be movably associated with the housing for operatively associating with the conductive pattern. The actuator may comprise an actuating member and a contact adapted to operatively associate with the conductive pattern. The contact may be in the form of a contact roller adapted to operatively associate with the conductive pattern. The roller may be formed of electrically conductive resilient material and may be biased into engagement with the electronic substrate. The contact may also be in the form of a contact plate having contact fingers adapted to operatively associate with the conductive pattern. The actuating member may be slidably associated with the electronic substrate.

The contact may be adapted to sequentially access the digital values of the conductive pattern when the actuating member is moved relative to the housing. A biasing member may further be associated with the actuating member for biasing the actuating member to a neutral position relative to the housing. The biasing member may act on the actuating member such that the user of the control device experiences increasing tactile resistance as the actuating member is moved relative to the housing. The biasing member may be further adapted to provide tactile resistance proportional to distance of movement of the actuator relative to the housing.

The electronic substrate and/or housing may comprise sound producing structures positioned to be engaged by the actuator for audibly indicating movement of the actuator relative to the housing.

The control device may be operatively connected to the injector via a fluid control module associated with the injector. The control device may further comprise a secondary actuator adapted to transmit a secondary fluid actuation signal to, for example, the fluid control module upon actuation. The secondary actuator may comprise a control button operatively associated with the electronic substrate for initiating the secondary fluid actuation signal.

A data communication cable may be associated with the electronic substrate for transmitting the digital values to the injector, either directly or indirectly. The data communication cable may be adapted to removably connect the control device with the injector, either directly or indirectly.

The housing of the control device may be a multi-piece housing including at least a first portion and a second portion. The first portion and second portion may be permanently joined together, for example, bonded together with an adhesive. The housing may be sized and shaped to be hand-held. A disposable sheath may enclose the respective pieces or portions forming the housing of the control device.

Another embodiment of the fluid delivery system is adapted to deliver multiple injection fluids to a patient and the control device may be used to control such a multi-fluid delivery system during medical procedures. In this embodiment, the fluid delivery system includes an injector for delivering multiple injection fluids to the patient. The control device is operatively associated with the injector and is adapted to control multi-fluid delivery from the multi-fluid delivery system. Accordingly, another embodiment of the control device generally comprises a housing, a first actuator associated with the housing, an electronic substrate disposed within the housing, and a second actuator associated with the housing and operatively associated with the electronic substrate. The electronic substrate comprises a conductive pattern and the first actuator is adapted to operatively associate with the conductive pattern when actuated by a user. The conductive pattern comprises a plurality of predetermined digital values corresponding to discrete flow rates of the injection fluids to be delivered by the injector desirably used in the multi-fluid delivery system such that when the first actuator is actuated, the first actuator operatively associates with the conductive pattern and transmits the digital values to the injector. In use, actuation of the second actuator initiates output signals to the injector desirably used in the multi-fluid delivery system corresponding to desired mixture ratios of the injection fluids to be delivered by the injector.

The first actuator may be movably associated with the housing for operatively associating with the conductive pattern. The digital values may be arranged such that the discrete flow rates are linearly proportional to distance of movement of the first actuator. Additionally, the digital values may be arranged such that the discrete flow rates incrementally increase with distance of movement of the first actuator. The incremental increase may comprise 5%, 10%, 20%, or any desired incremental increase with each digital value. The digital values typically include at least a first digital value corresponding to no movement of the first actuator and a 0% (i.e., no) discrete flow rate, and a last digital value corresponding to a maximum movement of the first actuator and a 100% (i.e., full) discrete flow rate. The last digital value may correspond to a maximum possible flow rate from the injector. The first actuator may comprise an actuating member and a contact roller adapted to operatively associate with the conductive pattern.

The second actuator may comprise a potentiometer, such as a linear potentiometer or a rotational potentiometer. Alternatively, the second actuator may comprise at least one push button. A second electronic substrate may be disposed within the housing and comprise a conductive pattern. The second actuator may be adapted to operatively associate with the conductive pattern on the second electronic substrate when actuated by the user. The fluid second actuator may also be movably associated with the housing and comprise an actuating member and a contact roller adapted to operatively associate with the conductive pattern on the second electronic substrate.

A method of controlling a fluid delivery system using the control device described generally hereinabove is also described in detail herein. The method may include operatively connecting the control device to the injector, with the control device adapted to control discrete flow rates of the injection fluid to be delivered by the injector to the patient and actuating the control device to transmit one or more predetermined digital values to the injector to control the discrete flow rates of the injection fluid delivered by the injector.

The control device, as indicated previously, may include an actuator and an electronic substrate comprising a conductive pattern. The actuator may be adapted for operative association with the conductive pattern and the conductive pattern may comprise a plurality of predetermined digital values corresponding to the discrete flow rates of the injection fluid to be delivered by the injector, such that the step of actuating the control device may comprise the actuator operatively associating with the conductive pattern to transmit one or more predetermined digital values to the injector.

The actuator may be movable relative to the conductive pattern, such that the step of actuating the control device may comprise moving the actuator relative to the conductive pattern. The actuator may comprise a contact operatively associated with the conductive pattern, such that when the actuator is moved relative to the conductive pattern the contact operatively contacts the conductive pattern. The contact may sequentially access the digital values when the actuator is moved relative to the conductive pattern. The contact may operatively contact the conductive pattern by rolling along the surface of the conductive pattern. The method may further comprise audibly indicating movement of the actuator relative to the conductive pattern.

The method may further comprise discontinuing actuation of the control device, for example, by releasing the actuator, such that the biasing member returns the actuator to a substantially pre-actuated position relative to the conductive pattern.

Furthermore, the control device may further comprise a secondary actuator adapted to transmit a secondary fluid actuation signal to the fluid delivery system, and the method may further comprise actuating the secondary actuator to transmit the secondary fluid actuation signal.

A variation of the method relates to controlling a multi-fluid delivery system comprising an injector in one example. In the alternative method, the method steps include operatively connecting a control device to the injector, with the control device adapted to control discrete flow rates of injection fluids to be delivered by the injector to a patient. Actuating a first actuator associated with the control device desirably transmits one or more predetermined digital values to the injector to control the discrete flow rates of the injection fluids delivered by the injector. Actuating a second actuator associated with the control device desirably initiates output signals to the injector corresponding to desired mixture ratios of the injection fluids to be delivered by the injector.

As noted in the foregoing, the control device desirably comprises an electronic substrate comprising a conductive pattern and the first actuator may be adapted for operative association with the conductive pattern. The conductive pattern, as noted, comprises, for example, a plurality of predetermined digital values corresponding to the discrete flow rates of the injection fluids to be delivered by the injector. Thus, the step of actuating the first actuator may comprise the first actuator operatively associating with the conductive pattern to transmit one or more predetermined digital values to the injector. As further noted in the foregoing, the first actuator may comprise a contact operatively associated with the conductive pattern, such that when the first actuator is moved relative to the conductive pattern the contact operatively contacts the conductive pattern. The contact may operatively contact the conductive pattern by rolling along the surface of the conductive pattern. The contact may sequentially access the digital values when the first actuator is moved relative to the conductive pattern.

Moreover, as also noted in the foregoing, a second electronic substrate may be disposed within the housing and comprise a conductive pattern. The second actuator may be operatively associated with the conductive pattern on the second electronic substrate during the step of actuating the second actuator. As an example, the contact may operatively contact the conductive pattern by rolling along the surface of the conductive pattern. Movement of at least one of the first actuator and the second actuator may be alerted to a user via a sensory indication, for example, tactile, visual, and/or auditory indications.

Further details and advantages will become clear when reading the following detailed description in conjunction with the accompanying drawings, wherein like reference numerals represent like elements throughout.

DETAILED DESCRIPTION

Figure 1:
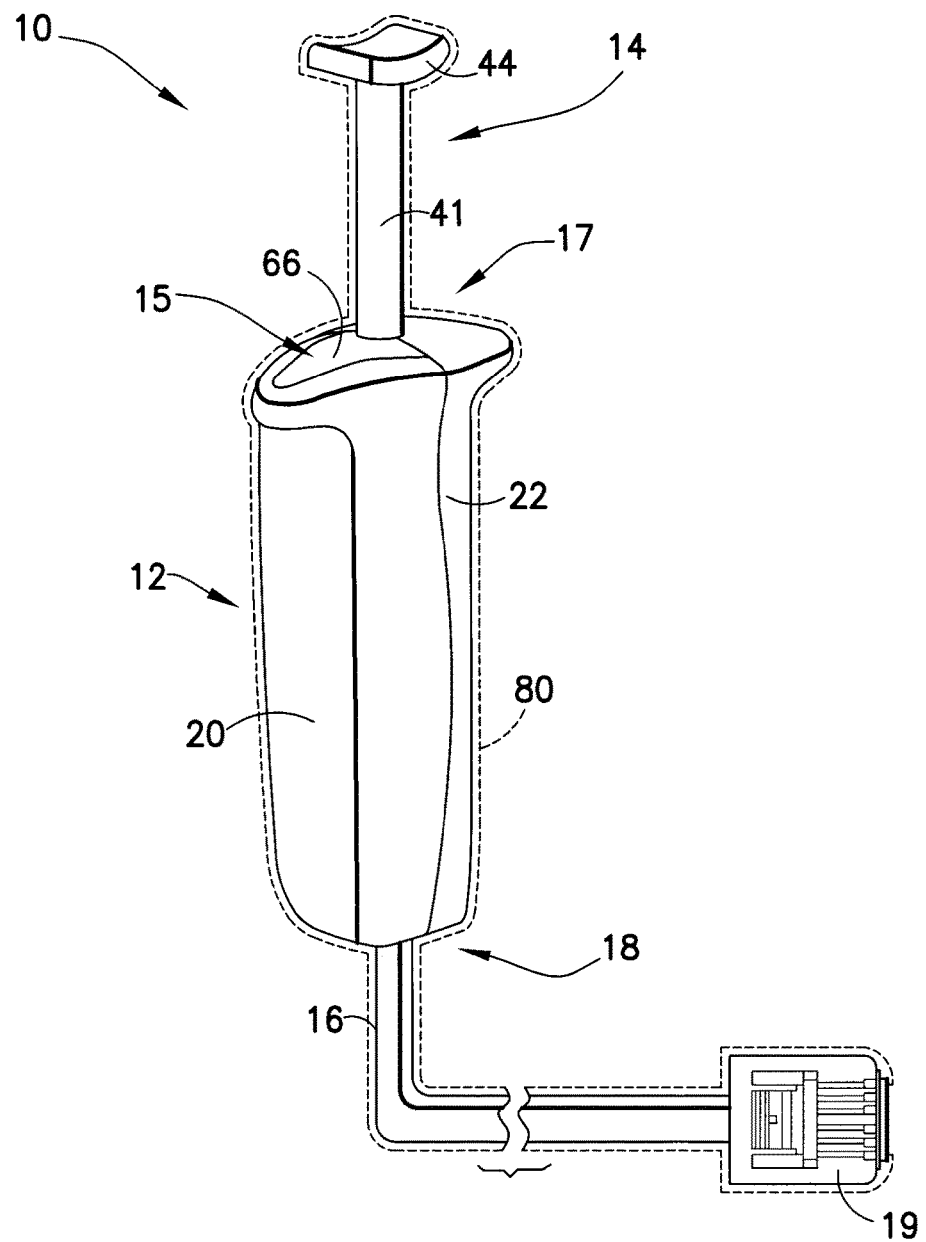
FIG. 1 is perspective view of a control device in accordance with one embodiment.

For purposes of the description hereinafter, spatial or directional terms, if used, relate to the embodiment, as it is oriented in the drawing figures. However, it is to be understood that the disclosure may assume various alternative variations, except where expressly specified to the contrary. It is also to be understood that the specific apparatus illustrated in the attached drawings, and described in the following description, are simply exemplary embodiments of the disclosure. Hence, specific dimensions and other physical characteristics related to the embodiments disclosed herein are not to be considered limiting.

Figure 2:
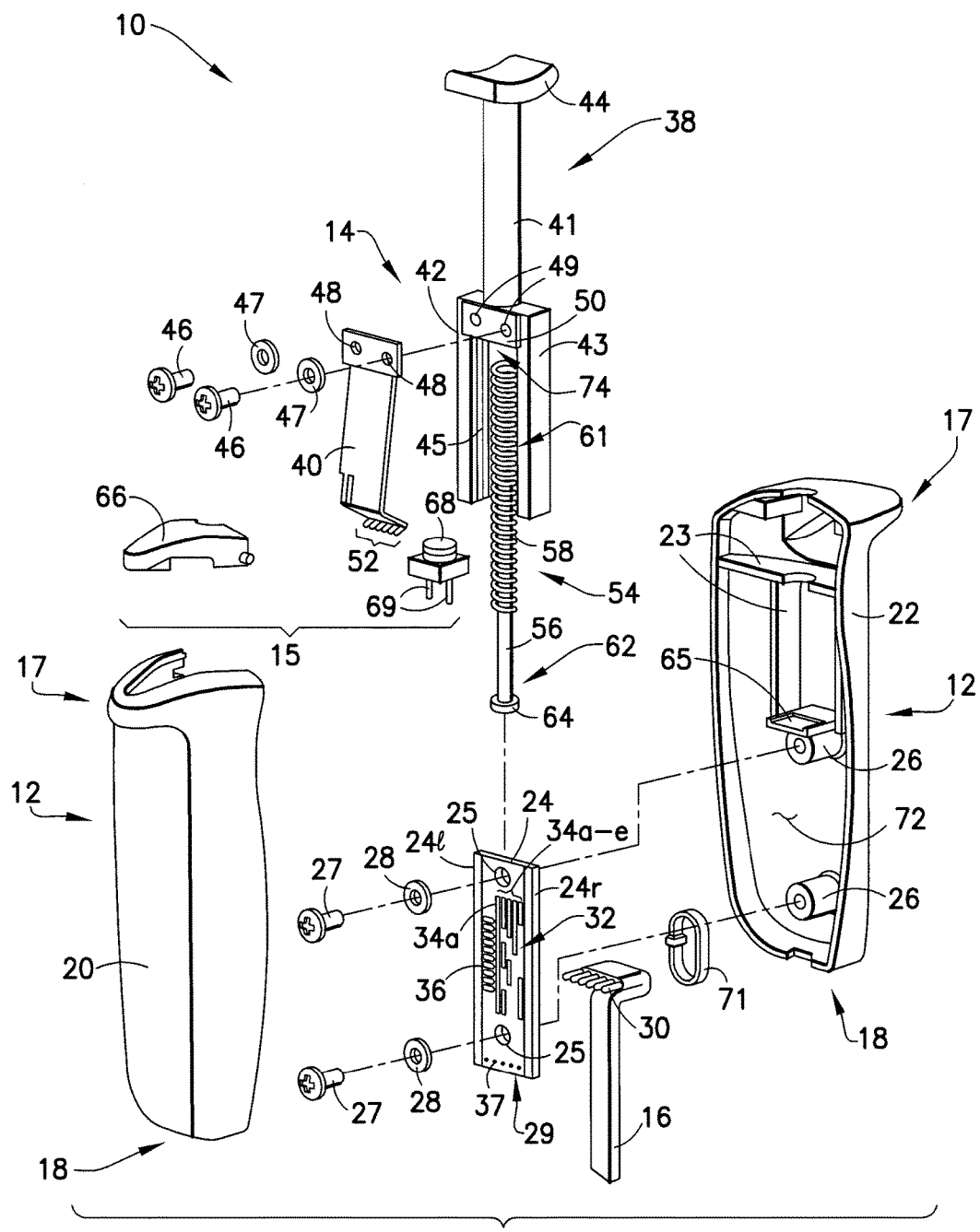
FIG. 2 is an exploded perspective view of the control device of FIG. 1.

A control device 10 according to one embodiment is illustrated in FIGS. 1 and 2. The control device 10 is desirably configured to be hand-held, and may be referred to herein as "hand controller 10". However, this form of the control device 10 is merely exemplary, and the hand controller 10 may be provided as a foot-controller or a robotic actuated device, as examples, or simply as an electronic console with one or more actuating devices, such as buttons, joysticks, and like elements.

Figure 4:
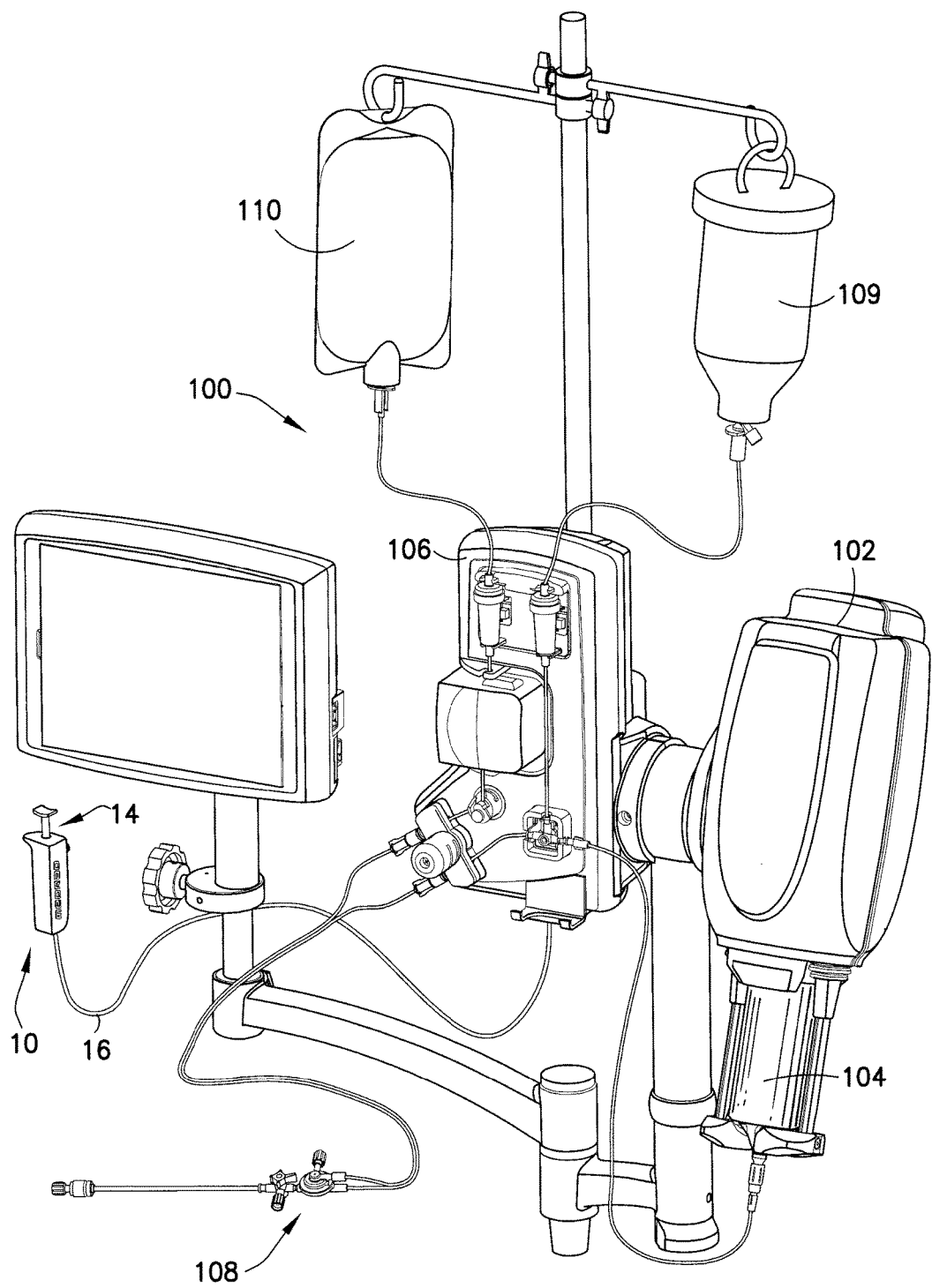
FIG. 4 is a perspective view of a fluid delivery system incorporating the control device of FIGS. 1 and 2.

The hand controller 10 is intended for use with an automatic fluid injection or delivery system 100, such as that generally illustrated in FIG. 4 discussed herein. The fluid delivery system 100 is used to deliver fluids to a patient during a medical injection procedure. For example, the fluid delivery system 100 may be used during an angiographic procedure to inject contrast media and common flushing agents, such as saline, into the body of a patient. An example of such a fluid injection or delivery system is disclosed in U.S. patent application Ser. No. 09/982,518, filed on Oct. 18, 2001, assigned to the assignee of the present application, the disclosure of which is incorporated herein by reference in its entirety. An additional example is disclosed in U.S. patent application Ser. No. 10/825,866, filed on Apr. 16, 2004, and entitled "Fluid Delivery System, Fluid Control Device, and Methods Associated with the Fluid Delivery System and Fluid Control Device", the disclosure of which is incorporated herein by reference in its entirety. The hand controller 10 is generally adapted to interface with one or more components of the fluid delivery system 100 to control the flow rates of the fluids, particularly contrast media in the case of angiographic procedures, to be delivered to the patient.

The hand controller 10 is generally adapted for electrical connection with the fluid delivery system 100 and controls the fluid delivery system 100 once the fluid delivery system 100 is appropriately programmed to accept input commands from the hand controller 10. More particularly, the hand controller 10 is adapted to digitally interface with the fluid delivery system 100 once associated therewith to deliver input commands to the fluid delivery system 100.

The hand controller 10 is further generally adapted to receive discrete physical inputs from a user or operator, select a predetermined digital value associated with each discrete physical input, and transmit the selected digital value to the fluid delivery system 100. The predetermined digital values or commands transmitted to the fluid delivery system 100 are converted into specific or discrete flow rate outputs from the fluid delivery system 100 which are delivered to the patient. Preferably, the digital values are proportional, for example, linearly proportional, to the user's physical inputs. The patient may be connected to the fluid delivery system 100 by means customary in the medical field, such as with a catheter.

With general reference to FIG. 1, the externally visible components of the hand controller 10 generally include a housing 12, an actuator 14 associated with the housing 12, a secondary actuator 15 also associated with the housing 12, and a cable 16 extending from the housing 12. The placement of these and any other components of the hand controller 10 are with reference to the presently illustrated embodiment and should not be construed as limiting.

Generally, the actuator 14 and the secondary actuator 15 are disposed at a top end 17 of the housing 12, and the cable 16 extends from a bottom end 18 of the housing 12. The housing 12 may have an ergonomic shape, so that the hand controller 10 may be comfortably held in either the left or right hand by a user, and to allow for single-handed operation thereof, as generally disclosed in U.S. patent application Ser. No. 10/237,139, filed on Sep. 6, 2002, assigned to the same assignee as the present application, the disclosure of which is incorporated herein in its entirety.

The housing 12 is desirably formed of plastic material, such as a suitable medical-grade plastic material. Inexpensive materials may be used for the housing 12 and the other components of the hand controller 10 to be discussed herein, so that the hand controller 10 may be a disposable item, disposed of, for example, after a preset number of procedures are conducted using the fluid delivery system 100. The housing 12 is formed to enclose and support the internal components of the hand controller 10 to be discussed herein. The hand controller 10 weighs in the range of about 0.25 to 1 pound, so that the hand controller 10 may be comfortably manipulated by an operator for extended periods of time without fatigue.

The cable 16 is generally adapted to transmit input commands in the form of digital values from the hand controller 10 to the fluid delivery system 100. The cable 16 may be any suitable type of cable adapted to digitally transfer the digital values to the fluid delivery system 100. For example, the cable 16 may be any suitable multiple-strand wiring cable, such as 6-pin phone cable. The cable 16 terminates in a connector 19 which is adapted to operatively and removably associate the hand controller 10 with the fluid delivery system 100. The connector 19 may be, for example, an RJ11 connector with six contacts which allows the end of the cable 16 distal or remote from the hand controller 10 to have a positive locking electrical connection with a component of the fluid delivery system 100.

With reference to FIGS. 1 and 2, the internal components of the hand controller 10 will now be discussed. The housing 12 includes at least a first portion and a second portion, such as a left side or portion 20 and a right side or portion 22, respectively. However, the housing 12 may include any number of pieces or components and is generally intended to be a multi-piece structure. The housing portions 20, 22 may include one or more internal rib structures 23 that provide structural support to the housing portions 20, 22, and support locations for supporting various internal components of the hand controller 10, as discussed herein. Since the hand controller 10 may be provided as a disposable device, as indicated previously, the housing portions 20, 22 may be permanently secured together with an adhesive bond or a permanent mechanical seal once the internal components of the hand controller 10 are assembled in place within the housing 12. Alternatively, the housing portions 20, 22 may be removably secured together by conventional mechanical fasteners (not shown). The housing portions 20, 22 are desirably formed of plastic material, for example, a suitable medical-grade plastic material. Any inexpensive plastic or non-plastic material may be used for the housing portions 20, 22, further facilitating the disposability of the hand controller 10.

The hand controller 10 further includes, internal to the housing 12, an electronic substrate 24, generally used to store the digital values to be transmitted via the cable 16 to the fluid delivery system 100. The electronic substrate 24 may be a conventional printed circuit board and is generally a rectangular structure that defines opposing top and bottom holes 25. The electronic substrate 24 is secured to bosses 26 integrally formed with the housing portion 22 of the housing 12 with conventional mechanical fasteners, such as screws 27 and washers 28. The body of the electronic substrate 24 defines one or more wire holes 29 for receiving one or more corresponding wires 30 of the cable 16 therein. The connection of the wires 30 with the wire holes 29 provides electrical connection and electronic data communication between the electronic substrate 24 and the fluid delivery system 100, once the connector 19 at the end of the cable 16 is connected to a component of the fluid delivery system 100. The electronic substrate 24 includes at least an equal number of wire holes 29 to the number of wires 30 in the cable 16.

Additionally, the electronic substrate 24 generally includes an electrical contact arrangement or conductive pattern 32 thereon. The conductive pattern 32 generally stores the digital values to be transmitted to the fluid delivery system 100. The digital values are in the form of binary values that generally correspond to specific or discrete flow rates to be delivered by the fluid delivery system 100 when the hand controller 10 is actuated, as discussed herein.

Generally, the conductive pattern 32, also referred to as a bit map herein, includes a plurality of columns, such as columns 34a-e, wherein each of the columns 34a-e includes at least one electrical contact and an adjoining space. Column 34a is a continual electrical ground contact and has no spaces. Thus, each of the columns 34b-e includes a combination of electrical contacts and spaces representing bit values, (i.e., 1 or 0). For example, from a top to bottom orientation in FIG. 2, column 34b includes an electrical contact, followed by a space, then followed by another electrical contact, which is then followed by yet another space, and finally, another electrical contact occupies the bottom of column 34b. In contrast, column 34d, for example, includes a single electrical contact that is followed by a single space. As shown in FIG. 2, each electrical contact and space in each of the columns 34b-e may be of various lengths.

A collinear horizontal grouping (i.e., row) of the electrical contacts and spaces includes the combination of either an electrical contact or a space from one or more of the columns 34b-e and electrical ground column 34a, with another electrical contact or space from another of the columns 34b-e. Thus, the conductive pattern 32 is generally divided into a plurality of collinear groupings (i.e., rows) of electrical contacts and spaces or bit values. The bit values for each of the columns 34b-e defines a specific "preprogrammed" digital or binary value that is to be transmitted to the fluid control module 106 when operatively accessed by the actuator 14. Each collinear grouping (i.e., row) corresponds to a predetermined gray code (i.e., a series of bit values). The predetermined or preprogrammed digital or binary values are desirably linearly arranged within the conductive pattern 32 and represent corresponding discrete flow rates to be delivered from the fluid delivery system 100. More specifically, the predetermined or preprogrammed digital or binary values within the conductive pattern 32 (i.e., collinear rows taken from top to bottom) preferably correspond to incrementally increasing discrete fluid flow rates to be delivered from the fluid delivery system 100 when the actuator 14 is actuated, for example, by the operator of the hand controller 10 moving the actuator 14 relative to the housing 12 as discussed herein. The gray code associated with the conductive pattern 32, as it relates to the delivery of flow rates from the fluid delivery system 100, may be generally as follows in Table 1:

TABLE 1

Gray Code & Flow Rate Assignment

| Gray Code | | | | Flow Rate |
|---|---|---|---|---|
| Bit 3 | Bit 2 | Bit 1 | Bit 0 | |
| 0 | 0 | 0 | 0 | 0% |
| 0 | 0 | 0 | 1 | 10% |
| 1 | 0 | 0 | 1 | 20% |
| 1 | 1 | 0 | 1 | 30% |
| 0 | 1 | 0 | 1 | 40% |
| 0 | 1 | 1 | 1 | 50% |
| 0 | 0 | 1 | 1 | 60% |
| 1 | 0 | 1 | 1 | 70% |
| 1 | 0 | 1 | 0 | 80% |
| 1 | 1 | 1 | 0 | 90% |
| 0 | 1 | 1 | 0 | 100% |

0 = corresponding bit connected to ground.
1 = corresponding bit open circuit.

The fluid delivery system 100 may utilize the foregoing gray code and the predetermined digital or binary values associated therewith to incrementally control the flow rate of the injection fluid (i.e., contrast media) in relation to a pre-programmed rate, such as 10 mL/s. For example, the predetermined digital or binary values may correspond to a predetermined volume per time rate, such as from 0 mL/s to the 10 mL/s rate, or a predetermined percentage rate of the pre-programmed rate, such as 0% to 100% of the 10 mL/s rate.

As is known in the relevant art, gray code does not necessarily have a subsequent increasing binary value incremented by a bit value in the proper mathematically logical progression. Therefore, each subsequent collinear grouping (i.e., row) of the conductive pattern 32 does not need to conform to standard increasing binary value representation. For example, a flow rate of 0% may be represented by a collinear grouping (i.e., row) of four (4) electrical contacts (i.e., 0000) at the top of the conductive pattern 32. Immediately below this collinear grouping (i.e., row), the subsequent collinear grouping (i.e., row) may have three electrical contacts followed by a single space (i.e., 0001), which may correspond to a flow rate of 10%. The next collinear grouping (i.e., row), corresponding to a flow rate of 20%, may have a space followed by two electrical contacts, followed by another space (i.e., 1001). As the foregoing illustrates, the collinear groupings (i.e., rows) from the top to the bottom of the conductive pattern 32 do not necessarily correspond to standard increasing binary value representation which would normally yield 0010 as the subsequent binary value for the 20% flow rate as an example.

In the present embodiment, the conductive pattern 32 includes eleven (11) collinear groupings (i.e., rows) to represent flow rates ranging from 0% to 100%. The first collinear grouping (i.e., digital or binary value) corresponds to no flow rate and the last collinear grouping (i.e., the 11$^{th}$ row) corresponds to 100% or maximum flow rate which may be the maximum flow rate possible from the fluid delivery system 100 or a preprogrammed maximum flow rate preprogrammed into or permitted by the fluid delivery system 100. The respective digital or binary values programmed in the conductive pattern 32 are accessed by the actuator 14, the details of which are discussed herein. Generally, the actuator 14 is movably associated with the housing 12, such that movement of the actuator 14 accesses the digital or binary values preprogrammed in the conductive pattern 32.

The electronic substrate 24 further includes sound producing structures 36 that are desirably adapted to indicate when movement of the actuator 14 has taken place. The sound producing structures 36 may be simple mechanical structures, such as ridges or grooves formed on the electronic substrate 24 which are engaged by the actuator 14 when the actuator 14 is moved relative to the housing 12. The sound producing structures 36 are generally disposed adjacent the conductive pattern 32, and may be arranged to correspond to the digital or binary values preprogrammed in the conductive pattern 32 (i.e., correspond to the collinear groupings).

Alternatively, the mechanical sound producing structures 36 may be replaced by an electronic sound producing device in generally the same location as the mechanical sound producing structures 36. The electronic sound producing device may be in the form of frequency modulators that correspond, respectively, to the preprogrammed digital or binary values in the conductive pattern 32. As indicated, the mechanical sound producing structures 36 or equivalent electronic sound producing device are configured to audibly indicate movement of the actuator 14. The electronic substrate 24 further includes a ground electrical contact 37 that is in electrical contact with a corresponding ground wire of the cable 16.

The actuator 14 generally includes an actuating member 38, generally in the form of a plunger which is movably associated with the housing 12 and a contact 40 that is generally adapted to operatively associate with the conductive pattern 32. The body of the actuating member 38 is formed with a rod portion 41 and depending slide rails 42, 43. The end of the rod portion 41 includes a finger pad 44 for the operator of the hand controller 10 to place his or finger, thumb or palm (i.e., with two fingers under the flange portion of housing portions 20, 22) to actuate the actuator 14. The slide rails 42, 43 are sufficiently spaced apart to slidably accommodate the electronic substrate 24 therebetween. In particular, the slide rails 42, 43 each define a guide track 45 for slidably receiving opposing lateral sides 24l, 24r of the electronic substrate 24 which enables the actuating member 38 to move up and down relative to the electronic substrate 24. The opposing guide tracks 45 defined by the respective slide rails 42, 43 preferably extend the length of the slide rails 42, 43.

The contact 40 is secured to the actuating member 38 by mechanical fasteners, such as screws 46 and cooperating washers 47. The screws 46 cooperate with holes 48 defined in the contact 40 and, further, may cooperate in a friction fit manner with corresponding holes 49 defined in an attachment plate or flange 50 connected to the actuating member 38 and generally extending between the slide rails 42, 43. The contact 40 further includes a plurality of contact fingers 52 for contacting the conductive pattern 32 on the electronic substrate 24. The contact fingers 52 are adapted to contact the preprogrammed digital or binary values (i.e., collinear groupings) on the electronic substrate 24. Generally, the actuator 14 accesses the preprogrammed digital or binary values when an operator of the hand controller 10 engages and depresses the finger pad 44 associated with the rod portion 41 which causes the actuating member 38 to depress into the housing 12. The contact 40 of the actuator 14 will progress sequentially from the first discrete digital or binary value (i.e., collinear grouping 1) to subsequent discrete digital or binary values (i.e. collinear groupings 2-11) as the operator presses downward on the finger pad 44. The contact fingers 52 establish the electrical connection with the respective digital or binary values which are transmitted to the fluid delivery system 100 via the cable 16. More specifically, the contact fingers 52 may contact either an electrical contact or a space in each of the columns 34b-e in the conductive pattern 32.

A biasing assembly 54 is associated with the actuator 14, and is disposed within the housing 12. The biasing assembly 54 is generally adapted to bias the actuator 14 against movement relative to the housing 12. The biasing assembly 54 is further adapted to provide increasing tactile resistance to the operator of the hand controller 10 the farther the actuating member 38 is moved (i.e., depressed into the housing 12). The biasing assembly 54 generally biases or tensions the rod portion 41 upward away from the electronic substrate 24.

The biasing assembly 54 generally includes a mandrel 56 associated with a compression spring 58. However, it will be apparent that suitable mechanically equivalent structures may be used in place of the mandrel 56 and compression spring 58 arrangement shown in FIG. 2, and discussed herein. The mandrel 56 generally has a first end 61 associated with the spring 58 and a second end 62 formed with an abutment flange 64. The abutment flange 64 is generally adapted to engage a corresponding surface or structure in the right portion 22 of the housing 12 which will allow the actuating member 38 to compress the spring 58 as the actuating member 38 is depressed into the housing 12 by the operator of the hand controller 10. For example, as shown in FIG. 2, one of the ribs 23 in housing portion 22 of the housing 12 may be formed with an engagement ledge 65 against which the abutment flange 64 contacts or rests to allow the actuating member 38 to compress the spring 58 as the actuating member 38 is depressed into the housing 12. The engagement ledge 65 may be recessed as illustrated in FIG. 2 to permit a mating engagement with the abutment flange 64.

The spring 58 is desirably configured such that the farther the actuating member 38 is depressed into the housing 12, the greater biasing force the operator of the hand controller 10 will experience. The first end 61 of the mandrel 56 is associated with the spring 58 and desirably acts as a spring-guide to prevent buckling of the spring 58 when the actuating member 38 is depressed.

The secondary actuator 15 is positioned generally adjacent the main actuator 14 and is generally adapted to provide an actuation signal to the fluid delivery system 100 to cause the fluid delivery system 100 to deliver a secondary injection fluid to the patient. Such a secondary fluid may include saline supplied from a source of saline associated with the fluid delivery system 100. Saline is a common flushing agent used during medical injection procedures such as angiography. The secondary actuator 15 generally includes a control button 66 operatively associated with a switch 68 having leads 69 which are connected to the electronic substrate 24, for example, by wires. The control button 66 is adapted for connection to housing portion 20 of the housing 12, such as by a pivotal connection therewith. The control button 66 is further generally adapted to contact or engage with the switch 68 when the control button 66 is depressed by the operator of the hand controller 10. Two switch wires (not shown) may connect the leads 69 to the wires holes 29 of the electronic substrate 24. Generally, when the operator of the hand controller 10 wants to initiate delivery of the secondary injection fluid, the operator depresses the control button 66 which engages the switch 68. The switch 68 then initiates the actuation signal which is transmitted to the fluid delivery system 100 via the electronic substrate 24 and the cable 16.

Figure 3:
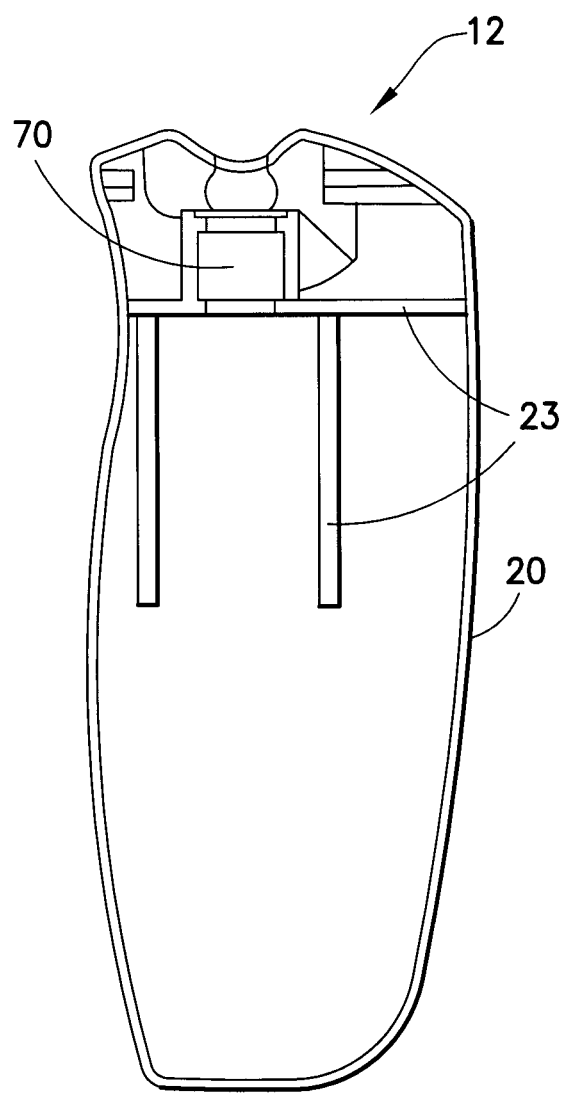
FIG. 3 is a side view of a housing of the control device of FIGS. 1 and 2.

With reference to FIGS. 2-4, one general method of assembling the hand controller 10 will now be discussed. Initially, the secondary actuator 15 may be assembled to the housing 12. This is accomplished by connecting the control button 66 with the left portion 20 of the housing 12 and positioning the switch 68 in a switch receiving pocket 70 defined by housing portion 20 of the housing 12. The switch receiving pocket 70 is defined by the internal rib structures 23 in housing portion 20 of the housing 12. The leads 69 from the switch 68 may then be associated with the electronic substrate 24 by suitable wiring.

Next, the wires 30 of the cable 16 may be secured in the corresponding wire holes 29 in the electronic substrate 24. A portion of the cable 16 will generally be retained within the right portion 22 of the housing 12, generally behind the electronic substrate 24. A cable tie 71 may be used to secure this portion of the cable 16 to provide strain relief. The tied portion of the cable 16 to be retained in housing portion 22 of the housing 12 is located in a cavity 72 defined by housing portion 22 of the housing 12. The electronic substrate 24 is used to secure the tied portion of the cable 16 when the electronic substrate 24 is secured to housing portion 22 of the housing 12 with screws 27 and washers 28.

The actuator 14 may be pre-assembled prior to being received in the housing 12. The actuator 14 is generally assembled by connecting the contact 40 to the attachment plate 50 extending between the slide rails 42, 43 with the screws 46 and cooperating washers 47. Thereafter, the biasing assembly 54 may be associated with the actuator 14. In particular, the compression spring 58 is placed about the mandrel 56 and the first end 61 of the mandrel 56 is located between the slide rails 42, 43, so that the compression spring 58 is in position to operatively associate with the actuating member 38. The slide rails 42, 43 generally define a receiving pocket 74 for the compression spring 58 and the first end 61 of the mandrel 56.

The actuator 14 and biasing assembly 54 may be placed in housing portion 22 of the housing 12 so that the abutment flange 64 on the mandrel 56 contacts the engagement ledge 65 defined by one of the internal rib structures 23 in housing portion 22. The actuator 14 is associated with the electronic substrate 24 as the actuator 14 is assembled in housing portion 22 of the housing 12 by receiving the opposing sides 24l, 24r thereof in guide tracks 45 defined in the slide rails 42, 43. The slidable engagement of the actuator 14 with the electronic substrate 24 allows the contact 40 of the actuator 14 to operatively associate with the conductive pattern 32. After applying a suitable adhesive to one or both of housing portions 20, 22 of the housing 12, the housing portions 20, 22 may be aligned, closed upon each other, and bonded together with adhesive or mechanical fastening.

With reference to FIGS. 1-4, the operation of the hand controller 10 will now be discussed according to the above-discussed embodiment. As indicated previously, the hand controller 10 is intended for use with the automatic fluid delivery system 100 which is generally illustrated in FIG. 4. The fluid delivery system 100 generally includes a powered injector 102 that is adapted to support and actuate a syringe 104 used to inject an injection fluid to a patient during a medical procedure, such as an angiographic procedure. The following operational discussion of the hand controller 10 will be with reference to an angiographic procedure involving the fluid delivery system 100 and how the hand controller 10 controls the delivery of the injection fluid from the fluid delivery system 100 to the patient. In typical angiographic procedures, the injection fluid is contrast media and such procedures typically further include saline as an additional or secondary injection fluid or flushing agent that is supplied to the patient.

The injector 102 is operatively associated with a fluid control module 106. The fluid control module 106 is generally adapted to support a fluid path set 108 that is generally adapted to fluidly connect the syringe 104 to a source of contrast media 109. The fluid path set 108 further connects the syringe 104 to a catheter (not shown) which is associated with the patient for supplying the contrast media and saline to the patient. The fluid path set 108 is further connected to a source of saline 110 which is supplied to the patient via the same catheter as the contrast media. The contrast media flow from the syringe 104 and the saline flow to the patient is regulated by the fluid control module 106 which controls the various valves and flow regulating structures in the fluid path set 108 to regulate the delivery of contrast media and saline to the patient based on the digital values provided by the hand controller 10. The hand controller 10 is shown connected to the fluid control module 106 in FIG. 4. However, the hand controller 10 could also be connected directly with the injector 102. The injector 102 and the fluid control module 106 are desirably in electronic data communication and the choice of associating the hand controller 10 with either the injector 102 or the fluid control module 106 primarily depends on the computer hardware and software associated with the injector 102 and/or the fluid control module 106. The injector 102 is generally used to supply the contrast media under pressure to the fluid path set 108 and, ultimately, the patient. The injector 102 is controlled by the hand controller 10 to supply the contrast media at discrete and preselected flow rates based on the physical inputs to the hand controller 10, as indicated previously.

To use the hand controller 10 with the fluid delivery system 100, the operator connects the cable 16 to the fluid control module 106 via the connector 19 at the end of the cable 16. The fluid control module 106 and injector 102 are programmed and set-up to receive input commands from the hand controller 10. Once the hand controller 10 is appropriately placed in electronic data communication with the fluid control module 106 and the injector 102 is appropriately primed with contrast media and/or saline, the operator may actuate the hand controller 10. It is assumed for the sake of expedience in explaining operation of the hand controller 10 that all necessary steps have been accomplished to fill the syringe 104 with contrast media and place the syringe 104 and the source of saline 110 in fluid communication with a patient via a catheter or other similar structure. Thus, the discussion herein regarding how the hand controller 10 controls the flow rate of contrast media and the supply of saline to the patient is with respect to an appropriately primed and programmed fluid delivery system 100.

To actuate the hand controller 10, the operator places his or her finger, thumb, or palm on the finger pad 44 disposed at the end of the rod portion 41 of the actuating member 38 of the actuator 14. As the actuating member 38 is depressed into the housing 12, the contact 40 moves from an initial, preactuated position generally associated with the first discrete digital or binary value in the conductive pattern 32 to another discrete digital or binary value, such as the second digital or binary value in the conductive pattern 32. The first discrete digital or binary position corresponds to a flow rate of 0% from the injector 102, and the second discrete digital or binary value corresponds, for example, to an incrementally increased flow rate of 10% flow rate from the injector 102. When the contact 40 of the actuator 14 is in the initial or preactuated position, the digital or binary value of 0% flow rate associated therewith is continuously transmitted to the fluid control module 106 via the cable 16 and which interfaces electronically with the injector 102, for example, by relaying the digital or binary value to the injector 102 which instructs the injector 102 not to actuate the syringe 104 and deliver fluid flow to the fluid path set 108. The biasing assembly 54 is associated with the actuator 14 as discussed in previously, and biases the actuating member 38 toward the initial or preactuated position, so that the initial or preactuated position of the actuating member 38 is the neutral or default position for the actuator 14, wherein no fluid flow is provided to the patient. Thus, if the operator for any reason discontinues pressure on the finger pad 44, the actuator 14 will automatically return to the neutral or default position where flow of contrast media is immediately discontinued.

When the contact 40 is in any other position with respect to the conductive pattern 32, the digital or binary value corresponding to that position is transmitted to the fluid control module 106 through the cable 16. It will generally be understood that as pressure is applied or released to the finger pad 44, the contact 40 will move freely up and down in contact with the conductive pattern 32, and output the various digital or binary values in the conductive pattern 32 to the fluid control module 106 which transmits the various digital or binary values as control signals to the injector 102. The injector 102 responds to the digital or binary values by supplying the contrast media at specific, discrete flow rates corresponding to a received digital or binary value until a new digital or binary values is received. Thus, the hand controller 10 generally takes an operator's physical inputs and selects or "looks up" a predetermined digital value associated with those inputs and digitally transmits the digital values to the injector 102 which responds to the digital values by delivering contrast media at pre-selected discrete flow rates corresponding to the digital values.

The hand controller 10 significantly improves over the prior art hand controllers, discussed previously, because the prior art hand controllers are limited to continuously converting user physical (i.e., analog) inputs to digital outputs, without any means or method of regulating or dampening the output from the injector. In practice, it is known that even experienced operators of angiographic injection apparatus may over-inject contrast media into a patient's body during such procedures. In contrast, the hand controller 10 is adapted such that in each position of the physical structure used to make inputs to the hand controller 10 (i.e., the actuator 14) the position directly corresponds to a discrete digital value with no analog to digital conversion required. As the operator makes physical inputs to the actuator 14, the injector 102 will respond with discrete, stepped changes in flow rate which are more easily monitored and controlled by the operator than the continuously variable flow rates provided by the prior art as shown and described, for example, in U.S. Pat. No. 6,221,045. The prior art hand control devices discussed previously can lead to large swings in flow rates delivered to the patient, and the possible over-delivery of contrast media.

At any time during the injection procedure, the operator may depress the secondary actuator 15 to deliver a saline flush to the patient. To initiate the saline flush, the control button 66 is depressed which initiates an actuation signal, for example, a saline start signal. Specifically, when the control button 66 is depressed, the control button 66 physically interacts with the switch 68 which initiates the actuation signal to the fluid control module 106. The actuation signal is transmitted via the electronic substrate 24 and the cable 16 to the fluid control module 106 which begins delivering saline from the source of saline 110 to the patient. If the primary actuator is actuated and the secondary actuator is then actuated or vice versa, the injector 102 will ignore the additional actuation. The secondary actuator 15 may be configured such that release of the control button 66 automatically ceases delivery of saline to the patient. Alternatively, the secondary actuator 15 may be configured such that a second depression of the control button 66 again will transmit a fluid stop signal to the fluid delivery system 100 which causes the fluid control module 106 to cease delivering saline.

It will generally be understood by those skilled in the art that the various signals transmitted by the hand controller 10 may be interpreted by the fluid control module 106 and/or injector 102 as either discrete flow or fixed flow signals depending on how the fluid control module 106 and/or injector 102 are initially programmed. For example, the discrete flow signals may range from 0% to 100% of the preprogrammed flow rate. Alternatively, the fixed flow control signal may be 60% of the preprogrammed flow rate, such that when the actuating member 38 is in any position past the initial or preactuated position a fixed flow signal is automatically transmitted to the fluid delivery system 100.

In order to maintain sterility and prevent contamination, the hand controller 10 may utilize a sterile sheath 80 (See FIG. 1), which is configured as a generally form-fittingly envelope enclosing at least the housing 12 of the hand controller 10. The sterile sheath 80 may enclose the actuator 14 and cable 16 as shown in dotted lines in FIG. 1. The sterile sheath 80 may be transparent and is not intended to impair any operator functions of the hand controller 10. This optional sterile sheath 80 may be made of inexpensive material, desirably plastic, and disposed after each use of the hand controller 10, extending the usable "disposable" life of the hand controller 10.

The hand controller 10, upon actuation of the actuator 14, generally provides a variety of physical and/or auditory cues for relaying to the operator an indication that the hand controller 10 is operational. In particular, the hand controller 10 is adapted to indicate to the operator the distance of movement or length of travel of the actuating member 38 within the housing 12 when the finger pad 44 is depressed by the operator. The distance of movement of the actuating member 38 will intuitively tell the operator how fast the flow rate of contrast media will be and, consequently, how much contrast media is being delivered to the patient by the injector 102.

The distance of movement may be audibly ascertained by the engagement of the contact 40 with the sound producing structures 36 (i.e., ridges or grooves) on the electronic substrate 24, or by engagement of the contact 40 with an equivalent electronic sound producing on the electronic substrate 24. The engagement of the contact 40 with the sound producing structures 36 will make a clicking sound or other audible cue, and the engagement of the contact 40 with the electronic sound producing device will make an electronically generated sound or tone. In each case, the sound produced will give an indication as to the length or distance of movement of the actuating member 38 relative to the housing 12 and, hence, the corresponding flow rate delivered by the fluid delivery system 100.

Additionally, the sound producing structures 36 are raised from or indented sufficiently into the electronic substrate 24 such that the engagement of the contact 40 with the sound producing structures 36 provides the operator with tactile feedback indicating the length, distance, or progression of movement of the actuating member 38 relative to the housing 12 (i.e., depression of the actuating member 38 in the housing 12). As generally indicated, the producing structures 36 may be formed as grooves, recesses, or indentations in the electronic substrate 24. Thus, the operator will experience tactile feedback that corresponds to the flow rate that will be delivered by the fluid delivery system 100 due to the engagement of the contact 40 with the sound producing structures 36.

Further, the biasing assembly 54 associated with the actuator 14 will provide immediate tactile feedback in the form of increasing resistive pressure as the actuating member 38 is depressed into the housing 12. Thus, the further the actuating member 38 is depressed into the housing 12, the more resistive force the operator will feel. The increasing resistance will provide immediate physical feedback that flow rate is increasing in the fluid path set 108 associated with the patient. The increasing resistance intuitively tells the operator that flow rate is increasing.

An alternative, second embodiment of the hand controller 10a is shown in FIGS. 5-9. The hand controller 10a is substantially functionally identical to the foregoing embodiment of the hand controller 10. The housing 12a of the hand controller 10a has the same external appearance as the housing 12 of the foregoing embodiment of the hand controller 10, and includes housing sides or portions 20a, 22a. The housing 12a is constructed of similar materials as the housing 12 in the foregoing embodiment. When the housing portions 20a, 22a are joined to enclose the internal components of the hand controller 10a, the visible components of the hand controller 10a, including the actuating member 38a, finger pad 44a, control button 66a, and cable 16a have generally the same external appearance as the forgoing embodiment of the hand controller 10. The internal components of the hand controller 10a have a slightly different configuration and arrangement from the foregoing embodiment of the hand controller 10, and these differences will now be discussed with reference generally to FIGS. 5-9.

Initially, it is noted that the cable 16a used in the hand controller 10a is identical to the cable 16 discussed previously. The housing portions 20a, 22a also include one or more internal rib structures 23a that provide structural support to the housing portions 20a, 22a, and support locations for supporting various internal components of the hand controller 10a. As with the foregoing embodiment, the rib structures 23a are generally adapted to support the internal components of the of the hand controller 10a in housing portion 22a of the housing 12a. However, it will apparent when comparing FIGS. 2 and 5 that the arrangement of the rib structures 23a is formed slightly differently from the rib structures 23 discussed previously. In both cases, however, the rib structures 23, 23a in housing portions 22, 22a are generally adapted to support the internal components of the hand controller 10a, as indicated.

Housing portion 22a of the housing 12a includes posts 204 in place of bosses 26. The posts 204 are adapted to mate or engage corresponding receptacles 206 formed internally in housing portion 20a of the housing 12a. The connection between the posts 204 and receptacles may be a compression friction fit. Thus, the housing portions 20a, 22a may be permanently secured together via a compression fit between the posts 204 and receptacles 206, once the internal components of the hand controller 10a have been assembled in place within the housing 12a.

The electronic substrate 24a of the hand controller 10a is analogous in construction and operation to the electronic substrate 24 of the first embodiment of the hand controller 10. Thus, the electronic substrate 24a includes the same conductive pattern 32a and wire holes 29a as found on the electronic substrate 24. However, unlike the previous electronic substrate 24, the current electronic substrate 24a lacks the sound producing structures 36. Additionally, the holes 25a defined in the electronic substrate 24a are now adapted to accept the posts 204 extending from housing portion 22a of the housing 12a to mount the electronic substrate 24a in position within housing portion 22a and within the housing 12a generally. The hand controller 10a also uses an analogous electrical connection between the control button 66a and the electronic substrate 24a. As with the control button 66 discussed previously, the control button 66a is adapted for a pivotal association with the housing 12a. However, the control button 66a is now adapted for pivotal association with housing portion 22a of the housing 12a rather than housing portion 20a of the housing 12a, as was the case in the hand controller 10. The cable 16a is electrically connected to the electronic substrate 24a by associating the wires 30a of the cable 16a with the wire holes 29a in the electronic substrate 24a.

Figure 5:
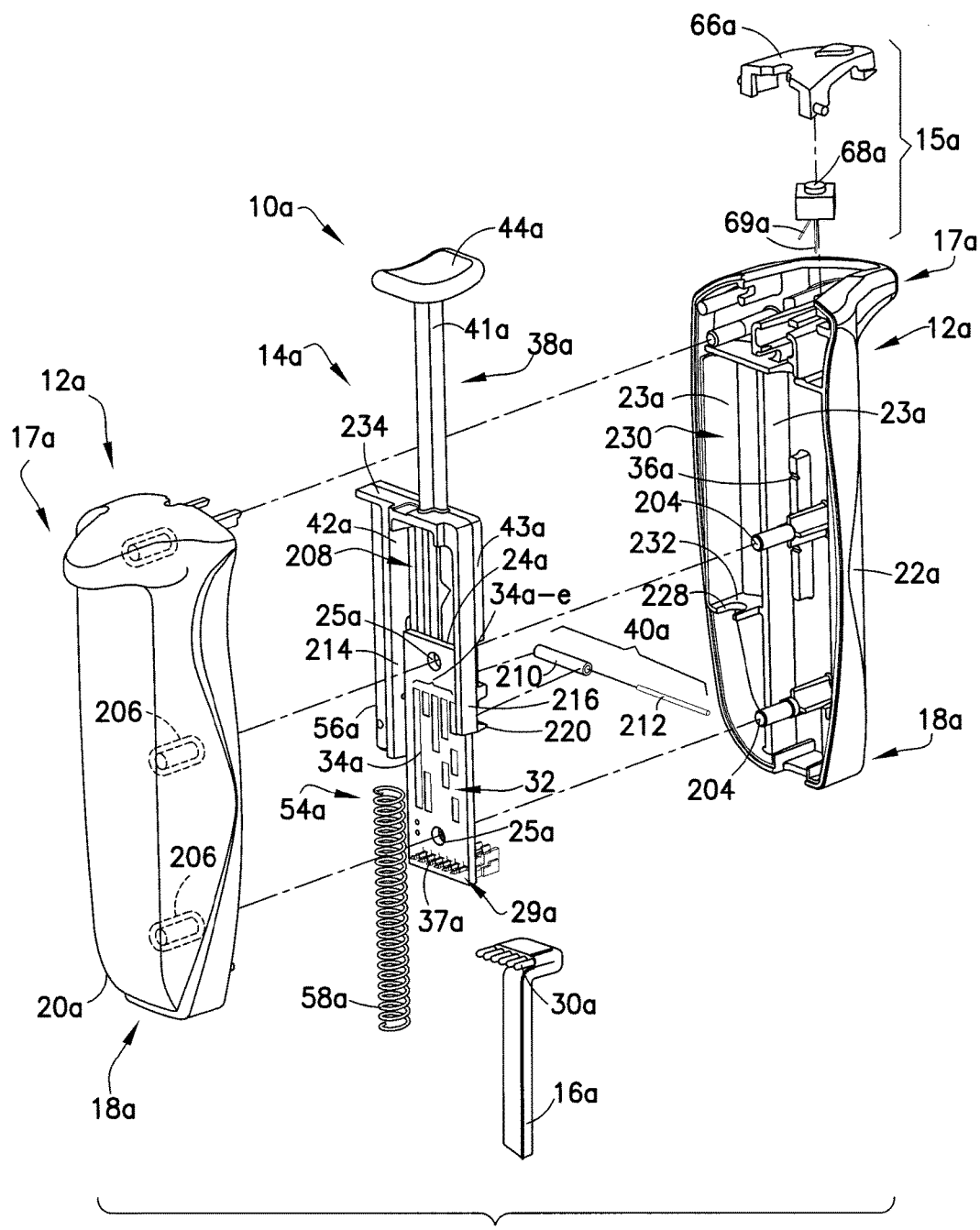
FIG. 5 is an exploded perspective view of an alternative embodiment of the control device.
Figure 6:
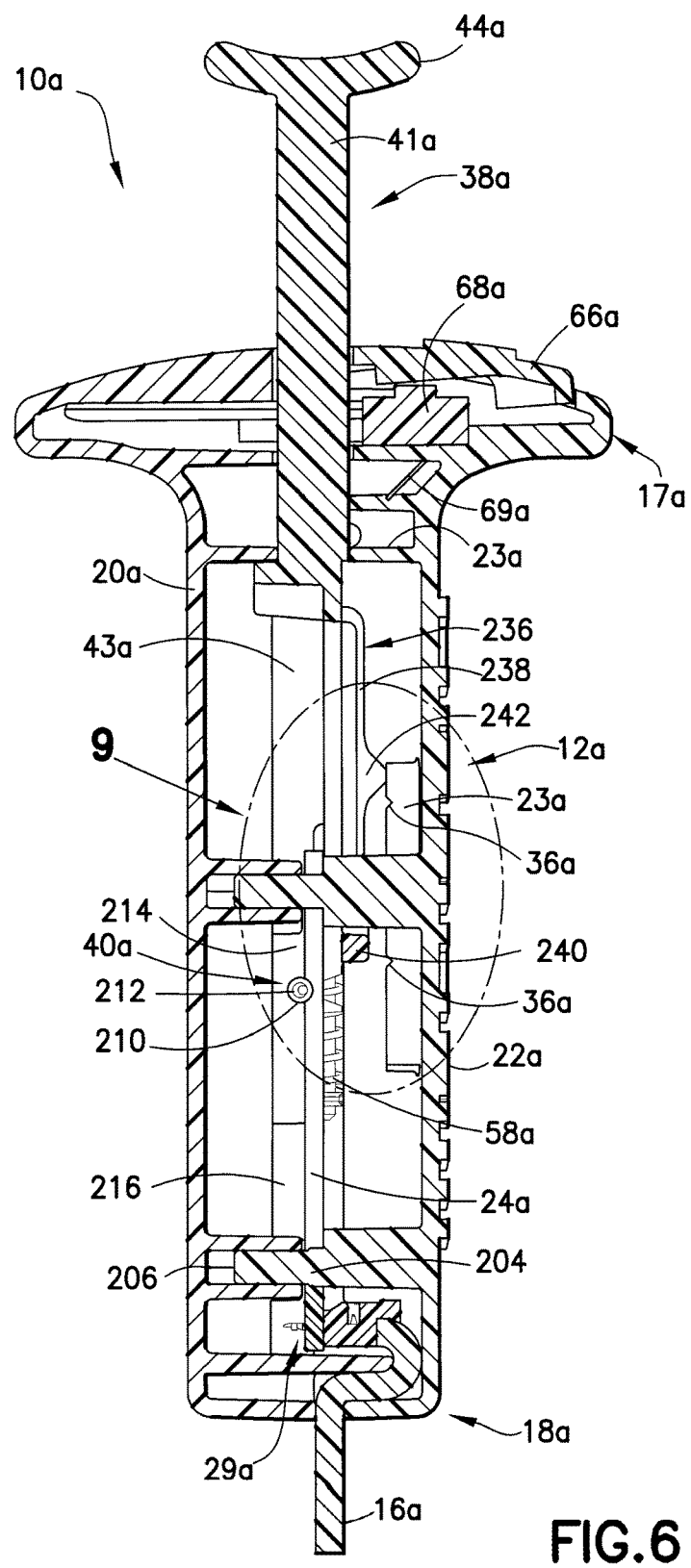
FIG. 6 is a left side and partial cross-sectional view of the assembled control device of FIG. 5.
Figure 7:
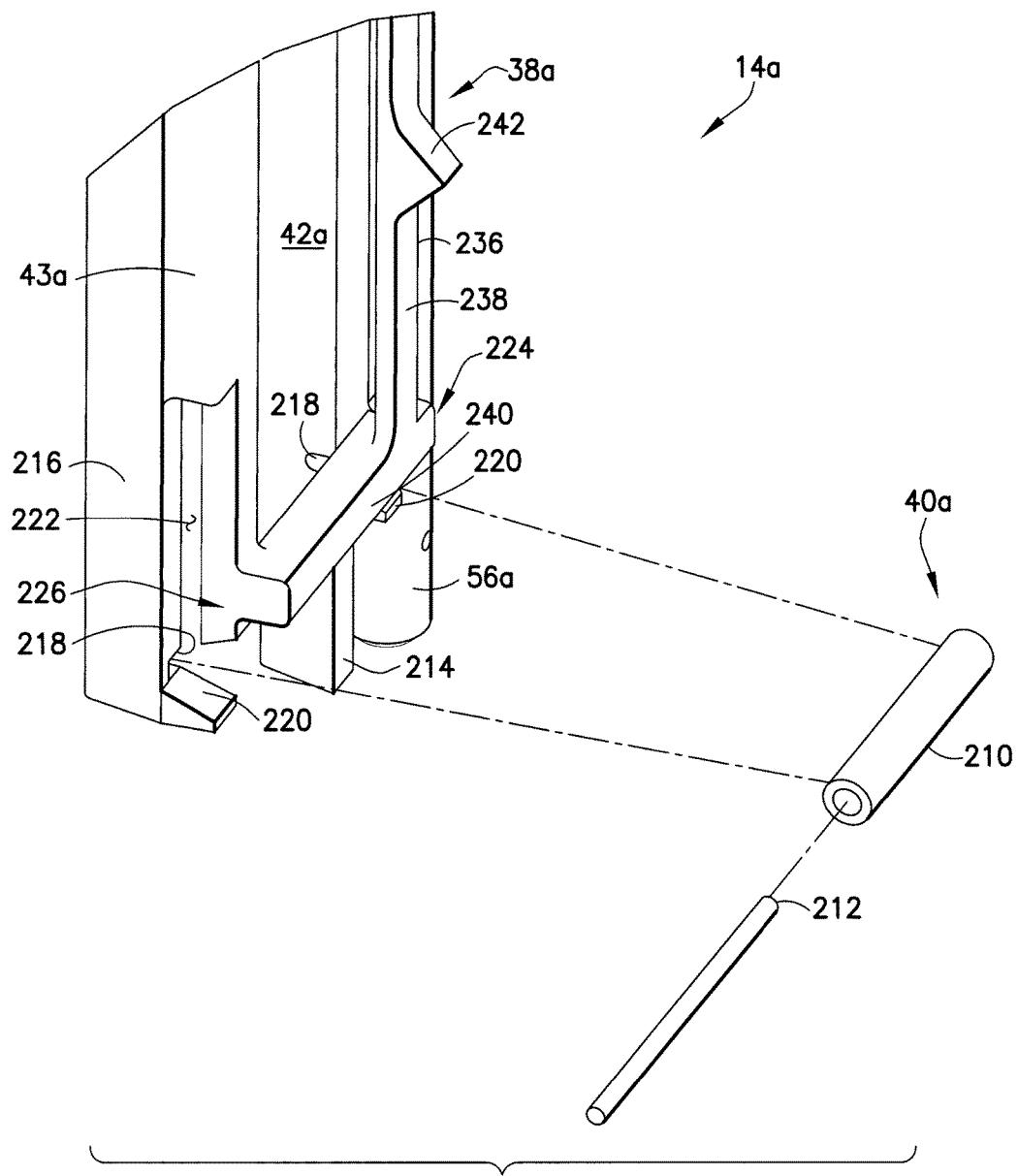
FIG. 7 is a perspective view of a bottom portion of an actuator of the control device of FIG. 5.
Figure 8:
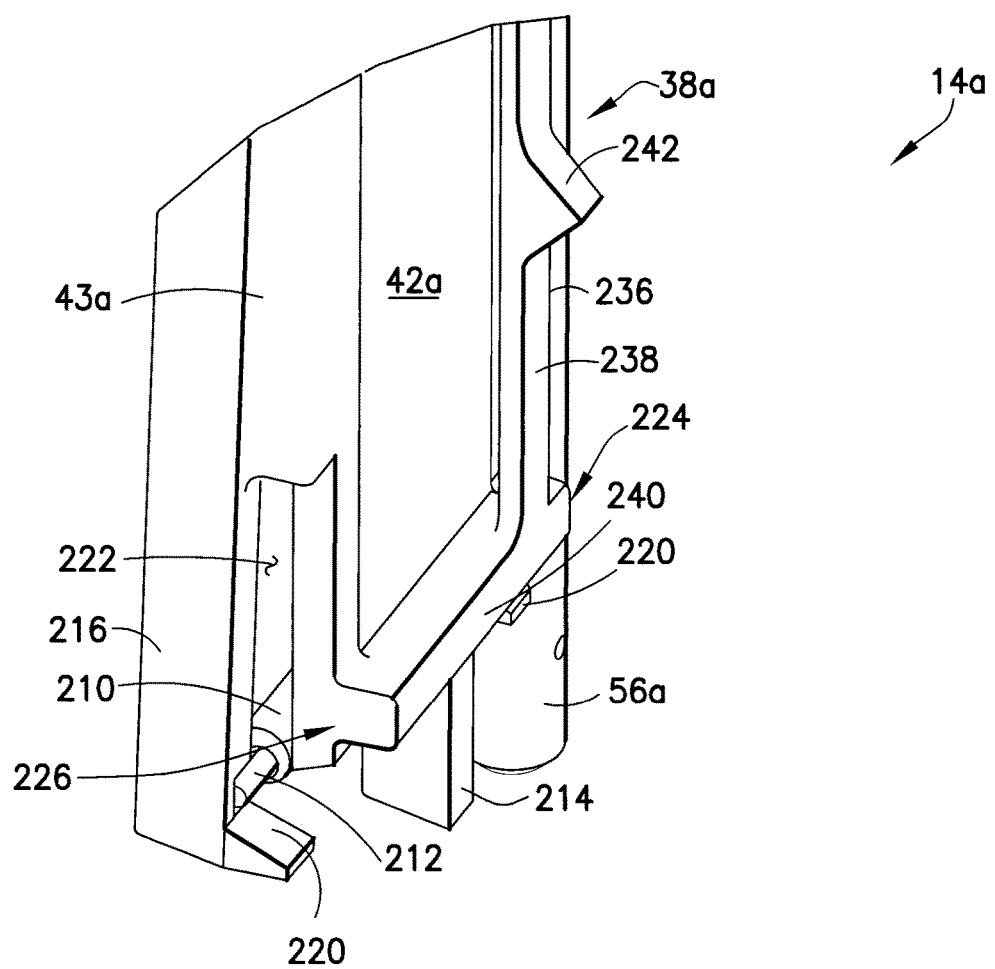
FIG. 8 is a perspective view of the bottom portion of the actuator of FIG. 5, showing a contact roller of the actuator.
Figure 9:
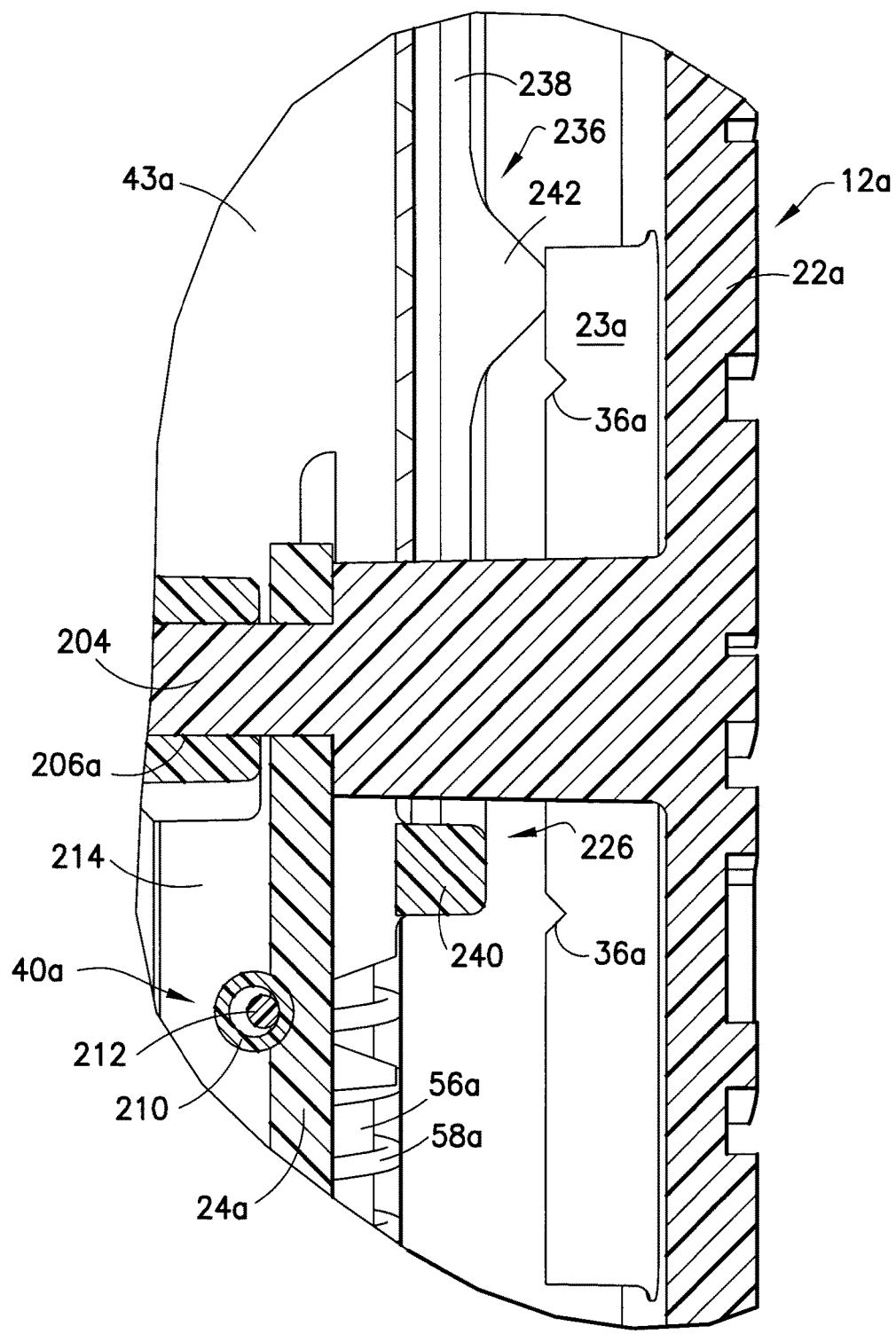
FIG. 9 is a detail and partial cross-sectional view of detail 9 in FIG. 6.

The sound producing structures 36a of the hand controller 10a are provided in a different location from the first embodiment of the hand controller 10. Specifically, the sound producing structures 36a are now provided on one of the rib structures 23a in housing portion 22a of the housing 12a. The sound producing structures 36a may again be formed as ridges or grooves. However, the sound producing structures 36a may further be formed as angled indents or recesses in the rib structure 23a as shown in FIGS. 5, 6, and 9. If the sound producing structures 36a are formed as ridges or similar raised structures, such raised structures may be formed as angled or pointed tabs on the rib structure 23a. Additionally, the "raised" version of the sound producing structures 36a may be formed integrally with the rib structure 23a, or provided as separate structures secured to the rib structure 23a. Additionally, the sound producing structures 36a may be provided in any convenient location within the housing 12a. For example, the sound producing structures 36a may be arranged within the same vertical plane and spaced in parallel relation to the electronic substrate 24a. As indicated previously, the sound producing structures 36a provide the user with an auditory and tactile indication of the actuation of the hand controller 10a. The sound producing structures 36a are physically engaged by a portion of the actuator 14a, as will be discussed further herein, to produce the auditory and tactile indications to the user. As further indicated previously, the sound producing structures 36a may be replaced by a generally equivalent electronic sound producing device.

The actuator 14a of the hand controller 10a has a similar overall external appearance to the actuator 14 discussed previously. However, the actuator 14a is configured to operatively associate with the conductive pattern 32 in a slightly different manner than the actuator 14 discussed previously. One difference between the actuator 14a and the actuator 14 discussed previously lies in the form of the contact 40a. An additional difference relates to the form and construction of the actuating member 38a of the actuator 14a and how the actuating member 38a supports the contact 40a. A further difference relates to the way the actuator 14a interacts with the sound producing structures 36a now disposed in housing portion 22a of the housing 12a. A still further difference relates to the location and configuration of the biasing assembly 54a of the actuator 14a. Each of the foregoing differences and others will be discussed in detail herein.

Beginning with the actuating member 38a, the actuating member 38a exhibits the same general "plunger" form and operation as the actuating member 38 discussed previously. The slide rails 42a, 43a of the actuating member 38a are spaced apart to accept the electronic substrate 24a therebetween. However, the slide rails 42a, 43a no longer define guide tracks 45 for slidably accepting the electronic substrate 24a. Accordingly, the side rails 42a, 43a will be referred to hereinafter simply as "rails 42a, 43a". The rails 42a, 43a define a generally rectangular-shaped receiving pocket 208 for accommodating the electronic substrate 24a. The rod portion 41a of the actuating member 38a is formed integrally with the rails 42a, 43a in a similar manner to the actuating member 38 discussed previously. Since the electronic substrate 24a is fixedly mounted on the posts 204 when the portions 20a, 22a of the housing 12a are joined together, the receiving pocket 208 is sized sufficiently to allow the actuating member 38a to move up and down relative to the electronic substrate 24a (i.e., slidably along the electronic substrate 24a).

The actuating member 38a is generally configured to support an alternative embodiment or variation of the contact 40 discussed previously. The contact 40 described previously is formed generally as a plate-like structure or member and is secured to the actuating member 38 with mechanical fasteners 46, 47. The contact 40 included contact fingers 52 for interacting with the electronic substrate 24 and sound producing structures 36.

In the present embodiment, the actuating member 38a is also configured to support the contact 40a, but the contact 40a now is in the form of a contact roller and will be referred to hereinafter as "contact roller 40a". The contact roller 40a includes a roller 210 rotatably mounted on an axle 212. The axle 212 is in turn rotatably supported by the actuating member 38a. In the present embodiment, the actuating member 38a is specifically adapted to rotatably support the contact roller 40a. The roller 210 is constructed of resilient and conductive material, such as conductive rubber. For example, the roller 210 may be a silicone based extruded elastomer having a silver-copper blend filing. However, the roller 210 may be made of any suitable conductive material, such as metal and, in particular, aluminum.

To support the contact roller 40a, the rails 42a, 43a of the actuating member 38a include extended support members 214, 216 adapted to rotatably support the axle 212. The support members 214, 216 may be integral, extended portions of the respective rails 42a, 43a. The support members 214, 216 define opposing notches or recesses 218 for rotatably supporting the ends of the axle 212. The support members 214, 216 further include guide tabs or ramps 220 disposed immediately adjacent the notches 218 to guide entry of the ends of the axle 212 into the notches 218 when the actuator 14a is assembled.

The support members 214, 216 define longitudinal gaps 222 with distal ends 224, 226 of the rails 42a, 43a. The longitudinal gaps 222 allow the respective support members 214, 216 to flex relative to the distal ends 224, 226 of the rails 42a, 43a when the contact roller 40a is mounted to the support members 214, 216 and engaged with the electronic substrate 24a. When the actuator 14a is assembled and mounted in place between the housing portions 20a, 22a of the housing 12a, the actuating member 38a including the rails 42a, 43a and support members 214, 216 are movable up and down within the housing 12a in the manner explained in detail previously in connection with the hand controller 10. However, due to the engagement of the roller 210 with the electronic substrate 24a in the present embodiment, the support members 214, 216 will be flexed outward (i.e., generally transversely) a small distance from the rails 42a, 43a and, more particularly, outward from the distal ends 224, 226 of the rails 42a, 43a. The "flexure" of the support members 214, 216 is caused by sizing the distance between the root of the notches 218 and the surface of the electronic substrate 24a slightly smaller than the diameter of the roller 210. As a result, when the axle 212 is mounted in the notches 218 and the electronic substrate 24a is fixed to the posts 204, the roller 210 through the axle 212 will cause the support members 214, 216 to flex or cantilever away from the distal ends 224, 226 of the rails 42a, 43a. This flexure applies a return or "back" pressure on the roller 210 through the axle 212. The back pressure on the roller 210 causes the resilient material of the roller 210 to deform and "mold" into engagement with the conductive pattern 32a on the electronic substrate 24a, resulting in a generally improved electrical contact between the contact roller 40a and conductive pattern 32a. The resiliency of the material forming the roller 210 and applied back pressure allows the roller 210 to accommodate height variances present in the electrical contacts or columns 34a-e forming the conductive pattern 32a. However, the back pressure is not significant enough to impede rotation of the roller 210 along the surface of the electronic substrate 24a.

The actuating member 38a and, by extension, the support members 214, 216 and rails 42a, 43a are made of a resiliently deformable or deflectable material such as plastic to allow for the flexure of the support members 214, 216. It will be generally understood that the back pressure or "flexure" force applied by the support members 214, 216 will be proportional to the flexibility of the material forming the actuating member 38a. The support members 214, 216 do not necessarily have to be formed integrally with the rails 42a, 43a and could be provided as separate elements that are secured to the rails 42a, 43a. Alternatively, since the support members 214, 216 are generally adapted to bias the roller 210 into engagement with the electronic substrate 24a, the support members 214, 216 could be replaced by a suitable mechanically equivalent biasing structure associated with the axle 212 and roller 210 to bias the roller 210 into engagement with the electronic substrate 24a. Such an arrangement could include one or more biasing elements, such as compression or leaf springs, associated with the axle 212 to bias the roller 210 into engagement with the electronic substrate 24a.

The contact roller 40a when biased into engagement with the electronic substrate 24a by the arrangement described hereinabove exerts a continuous and consistent pressure over the surface of the electronic substrate 24a and, specifically, the conductive pattern 32a. However, as indicated, the roller 210 is not impeded to a degree that would prevent the roller 210 from rotating on the axle 212 and rolling along the surface of the electronic substrate 24a based on inputs from the user or biasing assembly 54a to be discussed hereinbelow. As with the contact 40 discussed previously having contact fingers 52, the roller 210 of the contact 40a allows for selective shorting across the conductive pattern 32a to allow sequential access to the predetermined digital values in the conductive pattern 32a when the actuating member 38a is actuated by a user.

The biasing assembly 54a is provided in a different location from the biasing assembly 54 discussed previously, but includes the same general components as the earlier embodiment of the biasing assembly 54 and is functionally identical to the biasing assembly 54 discussed previously. The mandrel 56a is now formed integrally with the actuating member 38a. The mandrel 56a is located adjacent and generally parallel to rail 42a and is disposed substantially within housing portion 22a of the housing 12a when the hand controller 10a is assembled. However, the mandrel 56a may be associated with the actuating member 38a in any convenient location to allow for the biasing of the actuating member 38a to the neutral or no-flow position described previously in connection with the hand controller 10. The spring 58a is associated with the mandrel 56a in a similar manner to the mandrel 56 and spring 58 discussed previously. However, as will be clear when viewing FIG. 5, the mandrel 56a no longer engages a ledge formed on one of the rib structures 23a, but extends through a recess 228 defined in one of the rib structures 23a in housing portion 22a of the housing 12a. In particular, the rib structures 23a in the right portion 12a generally define an internal pocket 230 for receiving both the spring 58a and mandrel 56a. The bottom of the internal pocket 230 forms a ledge 232 for supporting one end of the spring 58a. The ledge 232 is similar in function to the ledge 65 described previously in connection with the hand controller 10. However, in the present embodiment, the spring 58a now acts between the ledge 232 and an upper cross member 234 of the actuating member 38a. Thus, when the mandrel 56a is moved downward in the internal pocket 230 as the actuating member 38a is depressed into the housing 12a by a user, the compression spring 58 is compressed within the internal pocket 230. The compression spring 58a provides a counteracting biasing force against the downward movement, and biases the actuating member 38a to the neutral or no-flow position discussed previously.

The actuating member 38a further includes an additional structure 236 for interacting with the sound producing structures 36a now provided on/in one of the rib structures 23a in the right portion 22a of the housing 12a. The "sound producing" structure 236 generally includes one longitudinal member 238 connected to the cross member 234 of the actuating member 38a and one transverse member 240 interconnecting the distal ends 224, 226 of the rails 42a, 43a. The transverse member 240 provides structural reinforcement to the distal ends 224, 226 of the rails 42a, 43a.

The longitudinal member 238 includes a raised tab (or detent) 242 that engages with the sound producing structures 36a. The tab 242 is angled or pointed to engage the raised, angled ridges or V-shaped indents or grooves forming the sound producing structures 36a. The raised ridges or V-shaped indents or grooves forming the sound producing structures 36a may be formed in a manner to generally correspond to the tab 242. The engagement of the tab 242 with the sound producing structures 36a will produce a distinct "clicking" sound as these elements engage one another. This engagement will also be tactilely apparent to the user of the hand controller 10a as the opposing tabs move over one another. Thus, the engagement of the tab 242 with the corresponding sound producing structures 36a provides both audible and tactile feedback to the user of the hand controller 10a during a fluid injection procedure. Other than the internal differences between the hand controller 10a discussed in the forgoing paragraphs, there is substantially no difference in operation between the two hand controllers 10, 10a.

As noted earlier in this disclosure, the concept of diluting contrast with saline is gaining in popularity in the medical imaging industry. For example, a medical practitioner for a diagnostic, interventional, or therapeutic procedure may be concerned with the amount of contrast media to be delivered to the patient, for example, if the patient has some preexisting condition that could lead to contrast-induced nephropathy and other medical complications. While the following discussion relates to the mixing of contrast and saline this should not be deemed limiting as the fluid delivery system 100 may be used to inject fluids other than contrast and saline. For example, in certain applications it may be desirable to "mix" a radiopharmaceutical fluid, for example, with saline and inject this mixture into a patient using the fluid delivery system 100. Accordingly, hand controllers 10, 10a may be adapted to allow the operator to dilute contrast media (or another fluid) to a point where radiographic images are still useful but also reduce the overall amount of contrast media delivered. Such a modification to hand controllers 10, 10a may be used in diagnostic, interventional, or therapeutic procedures so that valuable images are obtained while limiting the total amount of contrast delivered to the patient which, as indicated, may have particular advantage for more distressed patients (diabetics, etc.) undergoing such procedures.

As further indicated previously, such mixing may be real-time and the modified hand control devices 10, 10a may allow both real-time variability of flow rate and variability of contrast media/saline mix (or of any two desired fluids). The modified, mixing control devices 10, 10a, to be discussed herein, will interface with automatic fluid injection or delivery system 100 generally in the same manner described previously and system 100 will act upon the signals outputted by the control device 10, 10a to operate, for example, in a fully contrast delivery mode, fully saline delivery mode, or a hybrid mixing mode wherein contrast and saline (or any two or more fluids) are concurrently delivered to the patient in fixed ratios. For the purposes of illustration, several mixing control modifications 300 to control device 10a are described herein in connection with FIGS. 10-13. Each modification 300 is adapted provide the operator with the ability to control the ratio of contrast to saline via manual control apparatus desirably provided on the body of the control device 10a. However, it will be generally clear that each modification 300 maintains the previous operational characteristics associated with control device 10a. Similar modifications may be applied to control device 10 if desired.

Figure 10A:
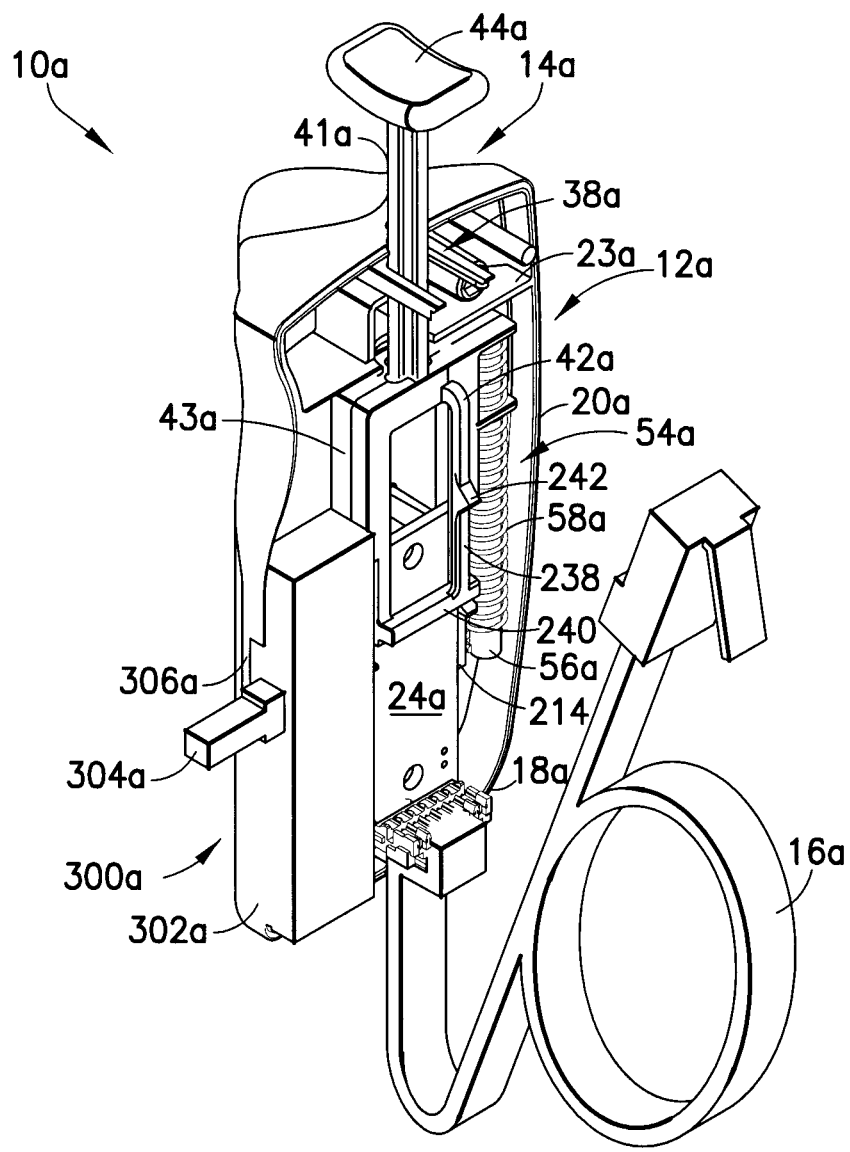
FIG. 10A is a perspective view of an embodiment of a control device adapted to control the mixing of multiple fluids and showing right side internal details thereof.
Figure 10B:
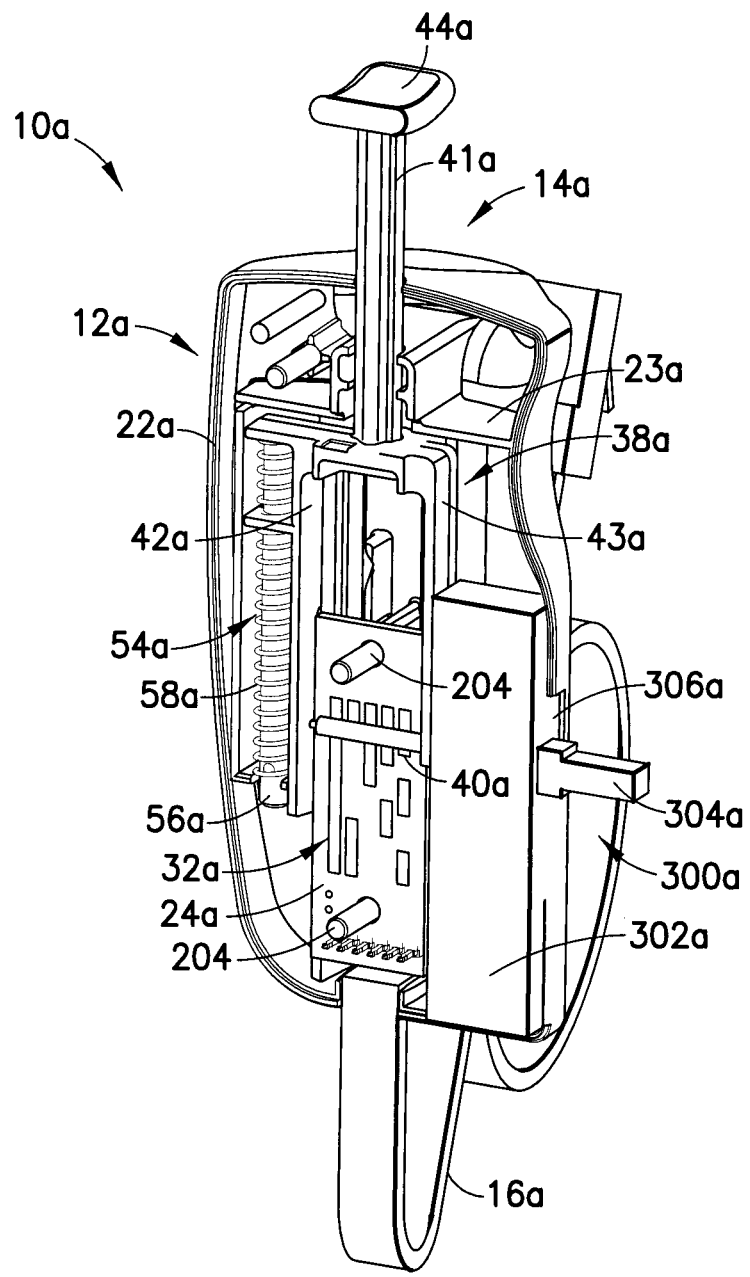
FIG. 10B is a perspective view of the control device of FIG. 10A showing left side internal details thereof.
Figure 10C:
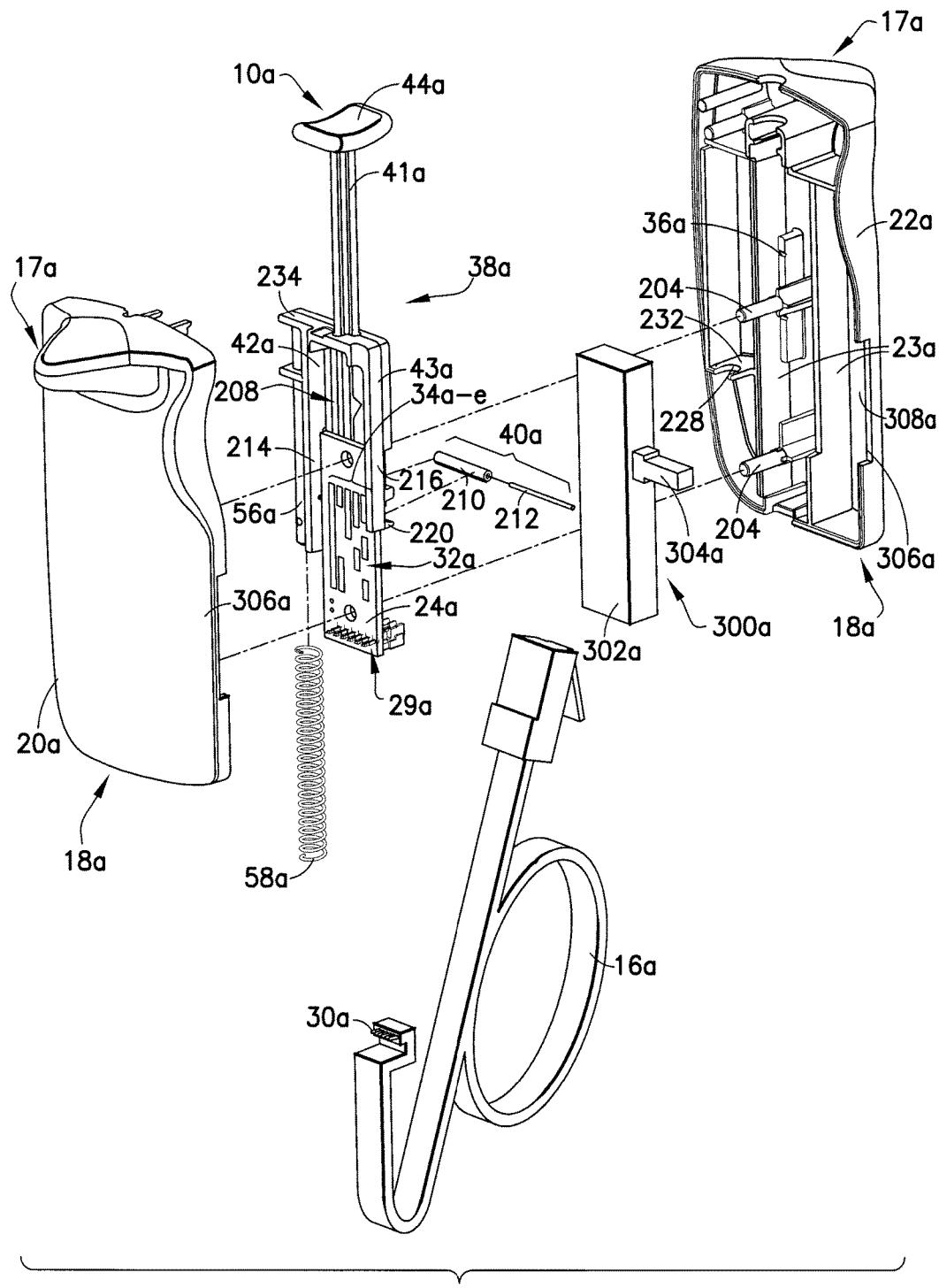
FIG. 10C is an exploded perspective view of the control device of FIG. 10A.

In a first modification 300a to control device 10a shown in FIGS. 10A-10C, the ratio of contrast to saline is controlled by a linear potentiometer 302a having a slider 304a. It will be understood that actuating member 38a operates in the manner described previously in this disclosure to control the overall flow rate of fluid delivered by fluid delivery system 100, which may be fully contrast, fully saline, or a mixture thereof. Linear potentiometer 302a is electrically connected to electronic substrate 24a. As is well-known in the electronics field, potentiometers are used to produce a variable amount of resistance depending on the position of a slider. In the present embodiment, the linear potentiometer 302a electrically interfaces with electronic substrate 24a so movement of the slider 304a produces a range of output signals from electronic substrate 24a that is outputted via cable 16a to the fluid delivery system 100 and instructs the same to operate, for example, in a contrast delivery mode, a saline delivery mode, and a "mixing" mode comprising contrast-saline mixture ratios defined by the position of the slider 304a. Such output signals may be continuously variable and interpreted continuously by the control unit(s) of the components of the fluid delivery system 100 and result in continuously variable changes in the contrast to saline mixture. Alternatively, such output signals may be discretely interpreted by the control unit(s) of the components of the fluid delivery system 100 in that movement of the slider 304a provides inputs to the electronic substrate 24a which will yield output signals that result in specified or predefined ratios of contrast to saline mixtures to be outputted from the fluid delivery system 100. In this latter operational mode, the fluid delivery system 100 and, more particularly, the control unit(s) of the fluid delivery system 100 discretely interprets the output signals from the electronic substrate 24a indicative of the incremental (or continuous) movement of the slider 304a as a specified mixture ratio of contrast to saline. In other words, the control unit(s) may interpret incremental (or continuous) movement as requests for incremental or discrete changes in contrast-saline mixture. The illustrated slider 304a may extend though a front opening 306a in housing 12a so as to be accessible by the operator's fingers. Housing portions 20a, 22a of housing 12a may together define a cavity 308a adjacent electronic substrate 24a for positioning the linear potentiometer 302a.

In exemplary operation, movement of the slider 304a all the way to the lower end of front opening 306a may result in a delivery of 100% contrast media from fluid delivery system 100 and opposite movement to the upper end of front opening 306a may yield 100% saline. Intermediate positions of slider 304a between these extremes may yield continuously variable ratios of contrast to saline mixtures or, alternatively, discrete ratios may be defined between these extremes. In like manner to that described previously, eleven exemplary discrete positions may be provided between the extremes of 100% contrast and 100% saline with each incremental or discrete position change resulting in, for example, a 10% change in the ratio mixture. For example, one discrete step or movement "up" by slider 304a from the lower end of front opening 306a may yield a 90% contrast and 10% saline mixture. A second discrete step or movement upward may yield an 80% contrast and 20% saline mixture, and so on. To further clarify, the control unit(s) of the delivery system 100 may have stored therein a series of predefined resistance values of linear potentiometer 302*a* which correspond to a variety of different contrast saline mixes. Accordingly, as a user continuously moves slider 304*a* between the lower end of front opening 306*a* and the upper end of front opening 306*a*, the control unit(s) will only instruct fluid delivery system 100 to change the ratio of contrast to saline when one of the predefined resistance values of linear potentiometer 302*a* is met. In this manner, continuous movement of slider 304*a* can be converted to discrete mixture ratios by the control unit(s). Tactile and/or auditory features much like that described in connection with detent 242 and sound producing structures 36*a* may be used to indicate each discrete change in mixture ratio with each discrete movement of the slider 304*a*.

Figure 11A:
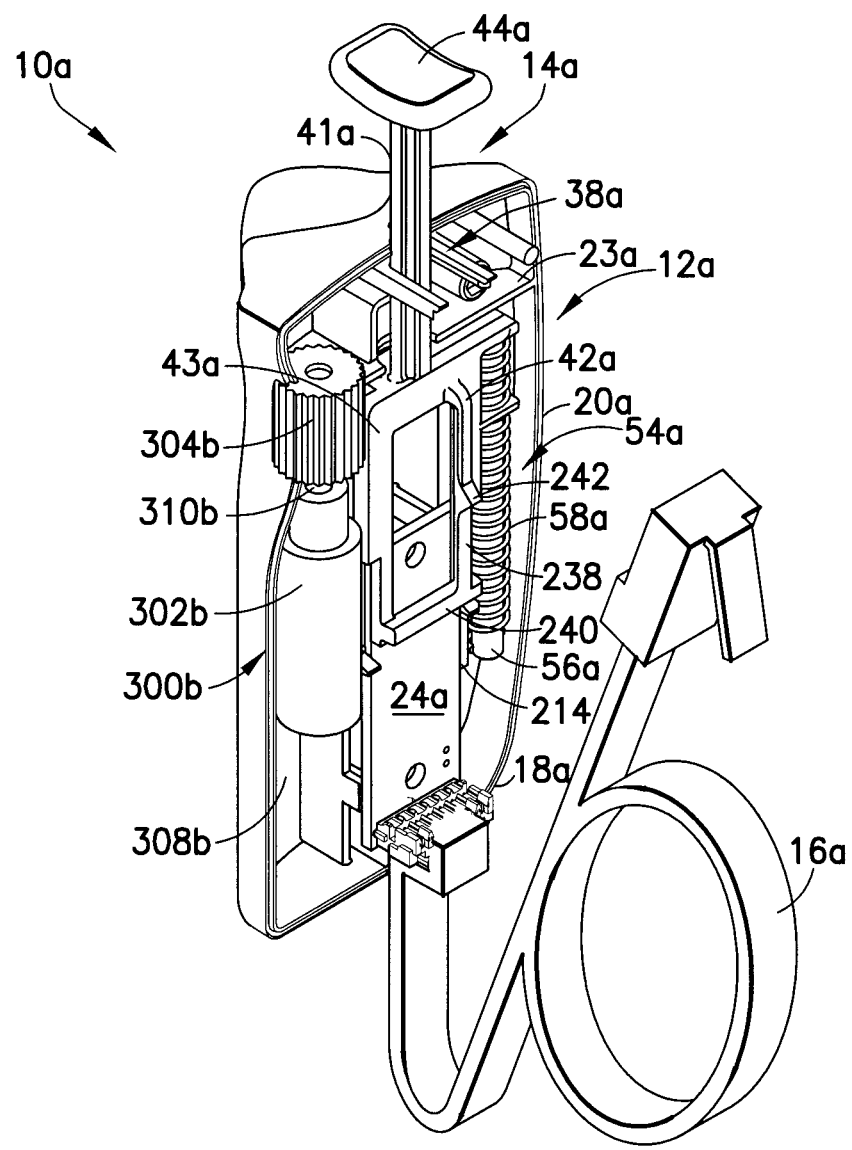
FIG. 11A is a perspective view of a second embodiment of a mixing control device and showing right side internal details thereof.
Figure 11B:
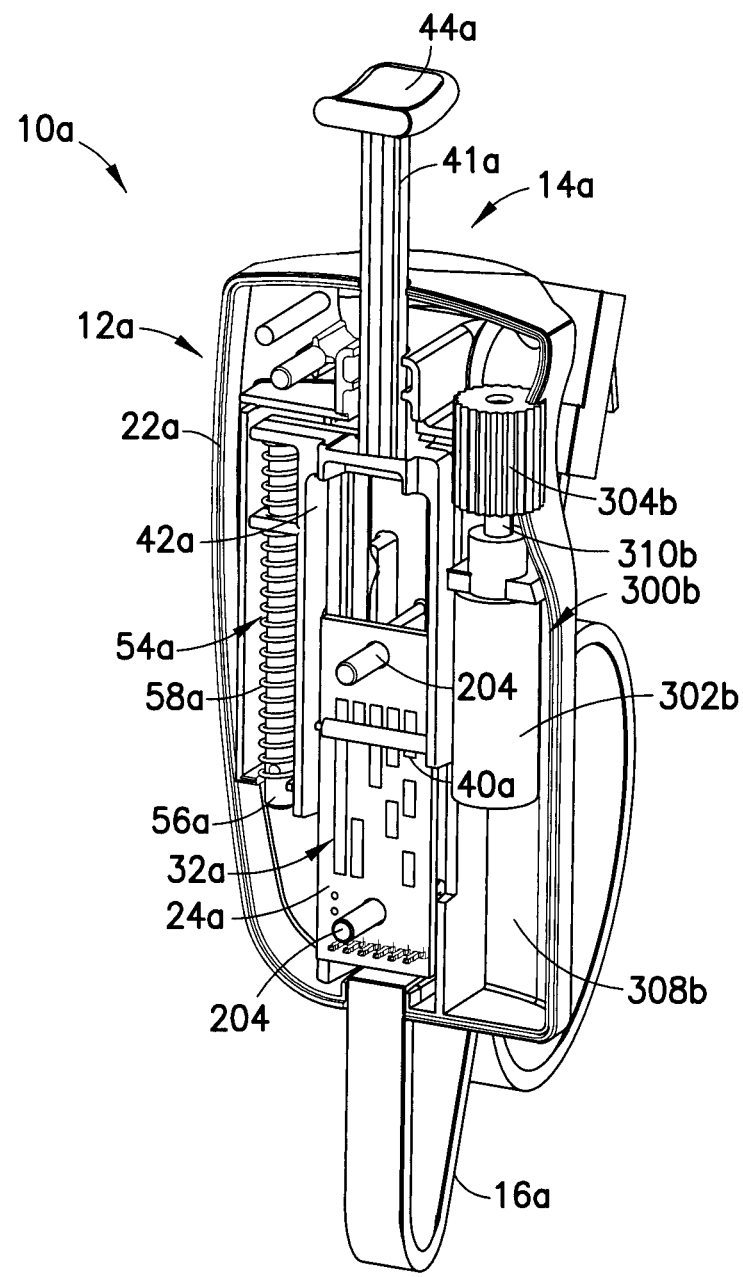
FIG. 11B is a perspective view of the mixing control device of FIG. 11A showing left side internal details thereof.
Figure 11C:
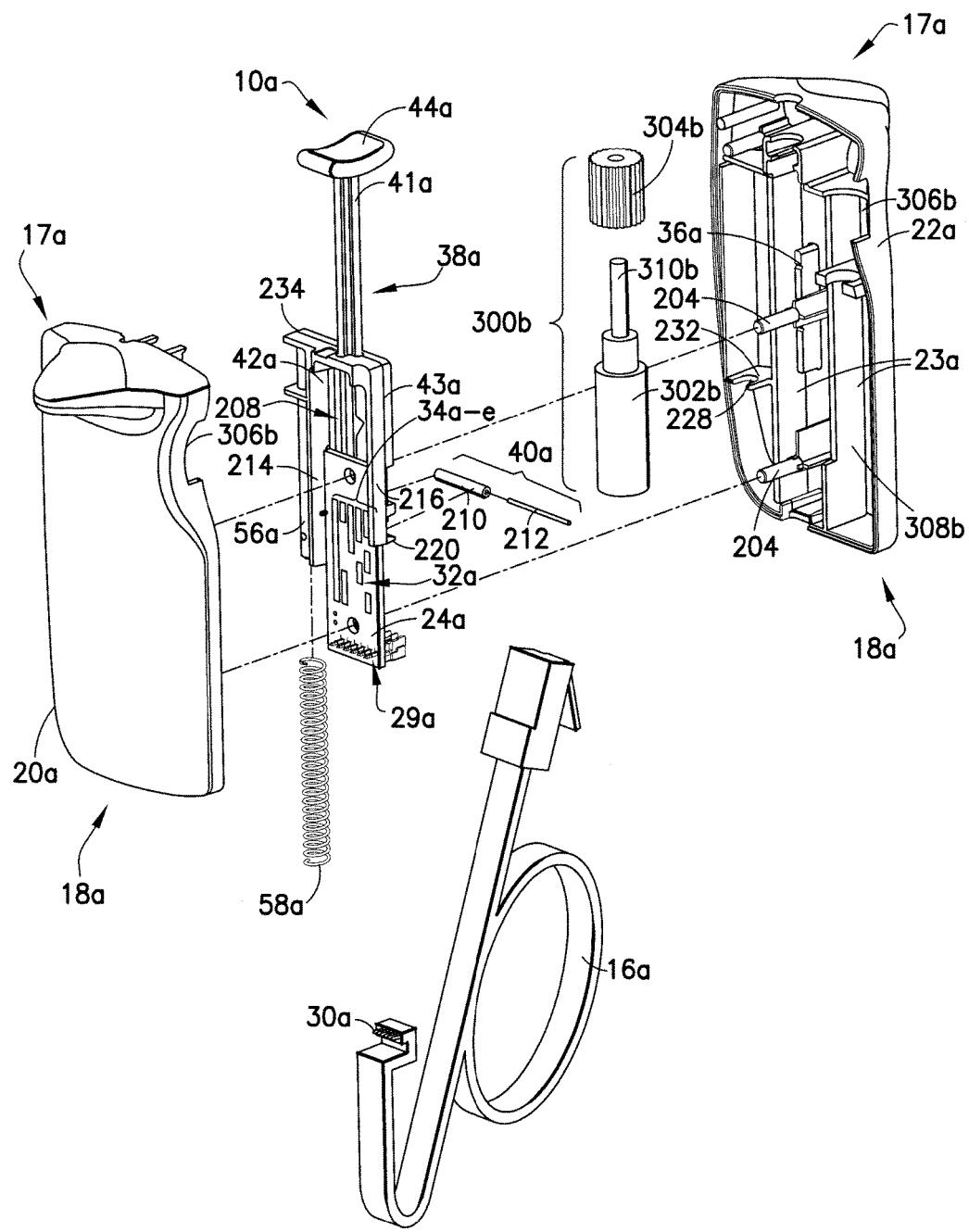
FIG. 11C is an exploded perspective view of the mixing control device of FIGS. 11A-11B.

FIGS. 11A-11C illustrate a second modification 300*b* to control device 10*a* wherein the ratio of contrast to saline is controlled by a rotational potentiometer 302*b* having a rotational dial 304*b*. As is well-known in the electronics field, rotationally potentiometers are used to produce a variable amount of resistance depending on the position of a shaft 310*b* supporting dial 304*b*. In the present embodiment, the rotational potentiometer 302*b* interfaces with electronic substrate 24*a* so rotational movement of the dial 304*b* produces a range of output signals from electronic substrate 24*a* that is outputted via cable 16*a* to the fluid delivery system 100 and instructs the same to operate, for example, in a contrast delivery mode, a saline delivery mode, and a "mixing" mode comprising contrast-saline mixture ratios defined by the rotational position of the shaft 310*b* supporting dial 304*b*. Such output signals may be continuously variable and interpreted continuously by the control unit(s) of the fluid delivery system 100 and result in continuously variable changes in contrast to saline mixture. Alternatively, such output signals may be discretely interpreted by the control unit(s) of the fluid delivery system 100 in that rotational movement of the shaft 310*b* supporting dial 304*b* provides inputs to the electronic substrate 24*a* which will yield output signals that result in specified or predefined ratios of contrast to saline mixtures to be outputted from the fluid delivery system 100. In this latter operational mode, the fluid delivery system 100 and, more particularly, the control unit(s) of the fluid delivery system 100 interprets the output signals from the electronic substrate 24*a* indicative of the incremental (or continuous) rotational movement of the shaft 310*b* supporting dial 304*b* as a specified mixture ratio of contrast to saline. In other words, the control unit(s) may interpret incremental or (or continuous) rotational movement as requests for incremental or discrete changes in contrast-saline mixture. The illustrated dial 304*b* may likewise extend though a front opening 306*b* in housing 12*a* so as to be accessible by the operator's fingers. Housing portions 20*a*, 22*a* of housing 12*a* may again define a cavity 308*b* adjacent electronic substrate 24*a* for positioning the rotational potentiometer 302*b*.

In exemplary operation, rotational movement of the rotational dial 304*b* all the way to one extreme may result in a delivery of 100% contrast media from fluid delivery system 100 and opposite rotational movement to the opposite extreme may yield 100% saline. Intermediate rotational positions of the dial 304*b* between these extremes may yield continuously variable ratios of contrast to saline mixtures or, alternatively, discrete ratios may be defined between these extremes in like manner to that described immediately above. To further clarify, the control unit(s) of the delivery system 100 may have stored therein a series of predefined resistance values of rotational potentiometer 302*b* which correspond to a variety of different contrast saline mixes. Accordingly, as a user continuously moves dial 304*b* in front opening 306*b*, the control unit(s) will only instruct fluid delivery system 100 to change the ratio of contrast to saline when one of the predefined resistance values of rotational potentiometer 302*b* is met. In this manner, continuous rotational movement of dial 304*b* can be converted to discrete mixture ratios by the control unit(s). Tactile and/or auditory features much like that described in connection with detent 242 and sound producing structures 36*a* may be used to indicate each discrete change in mixture ratio with each discrete movement of the dial 304*b*.

Figure 12A:
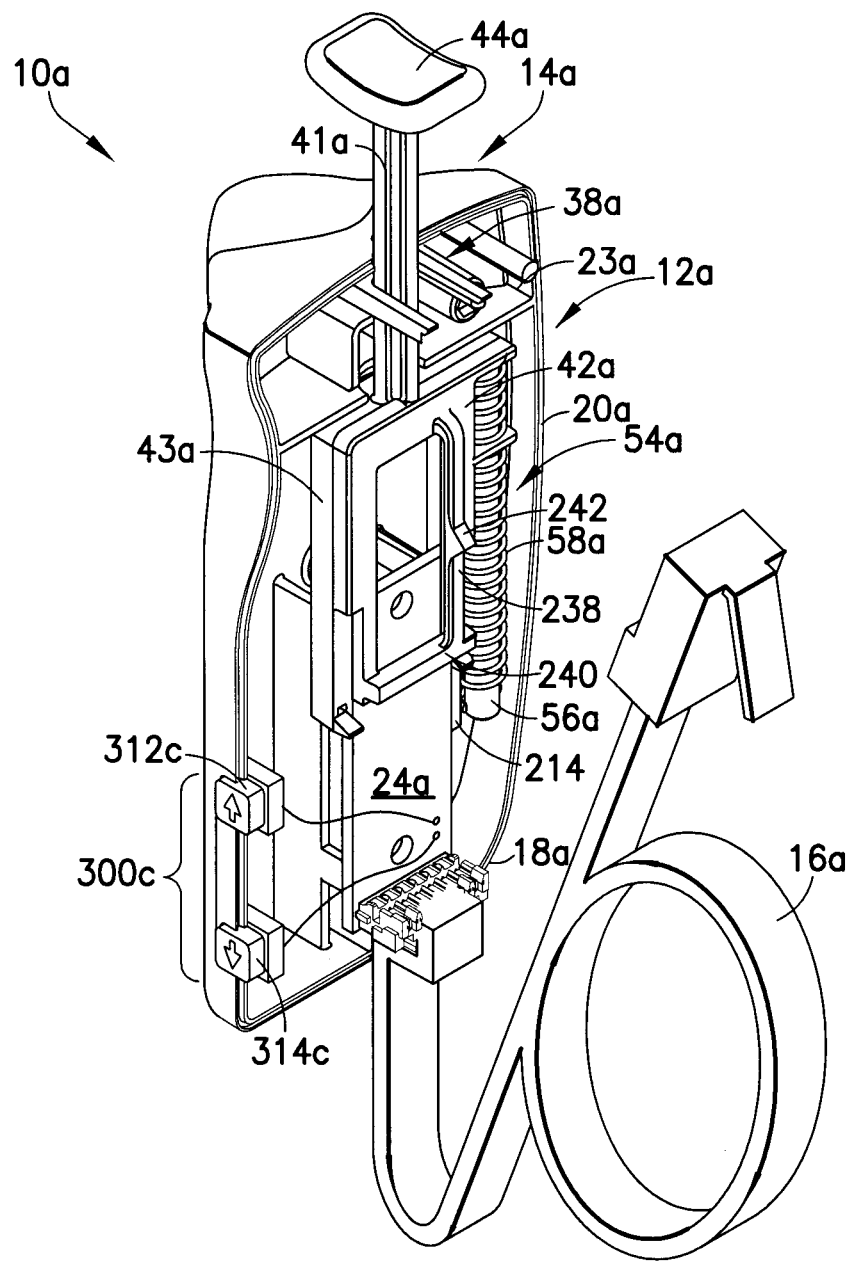
FIG. 12A is a perspective view of a third embodiment of a mixing control device and showing right side internal details thereof.
Figure 12B:
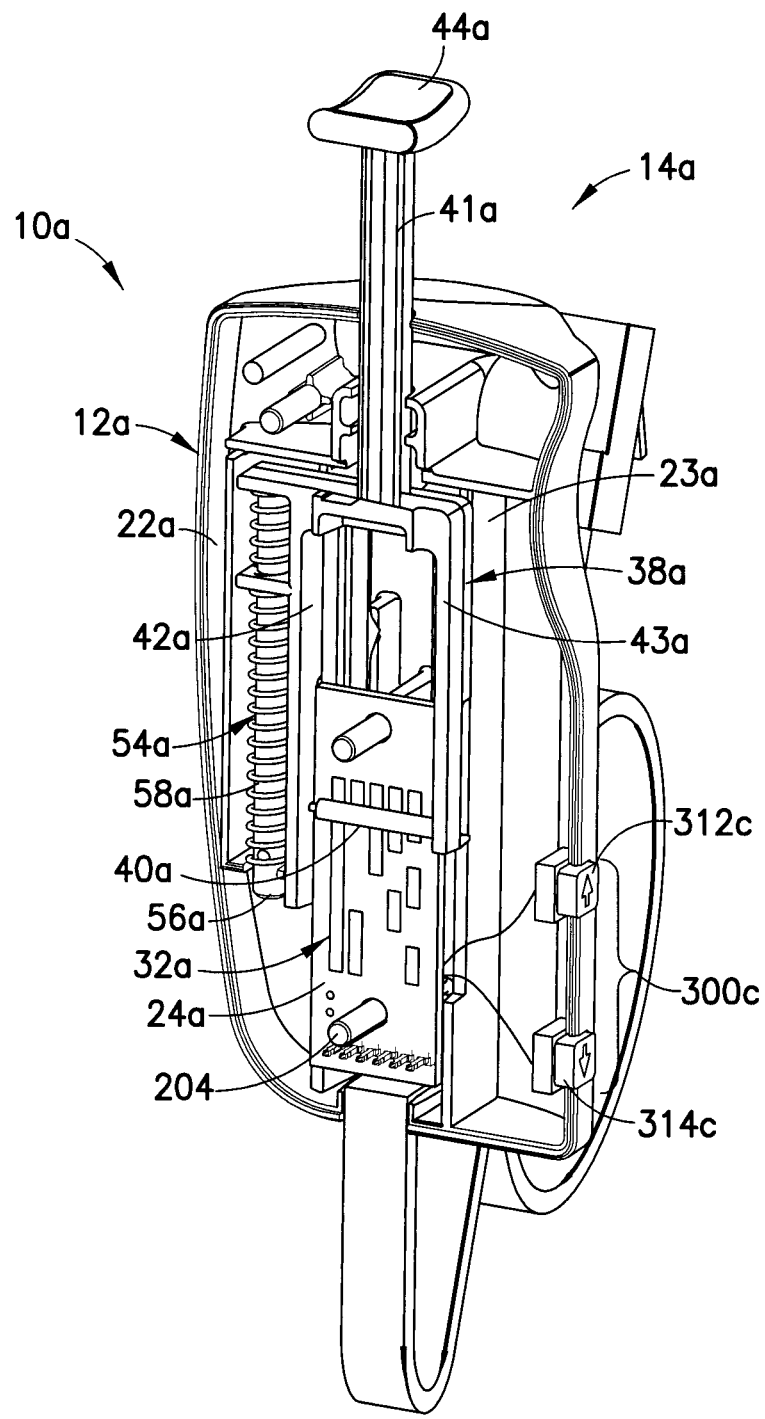
FIG. 12B is a perspective view of the mixing control device of FIG. 12A showing left side internal details thereof.
Figure 12C:
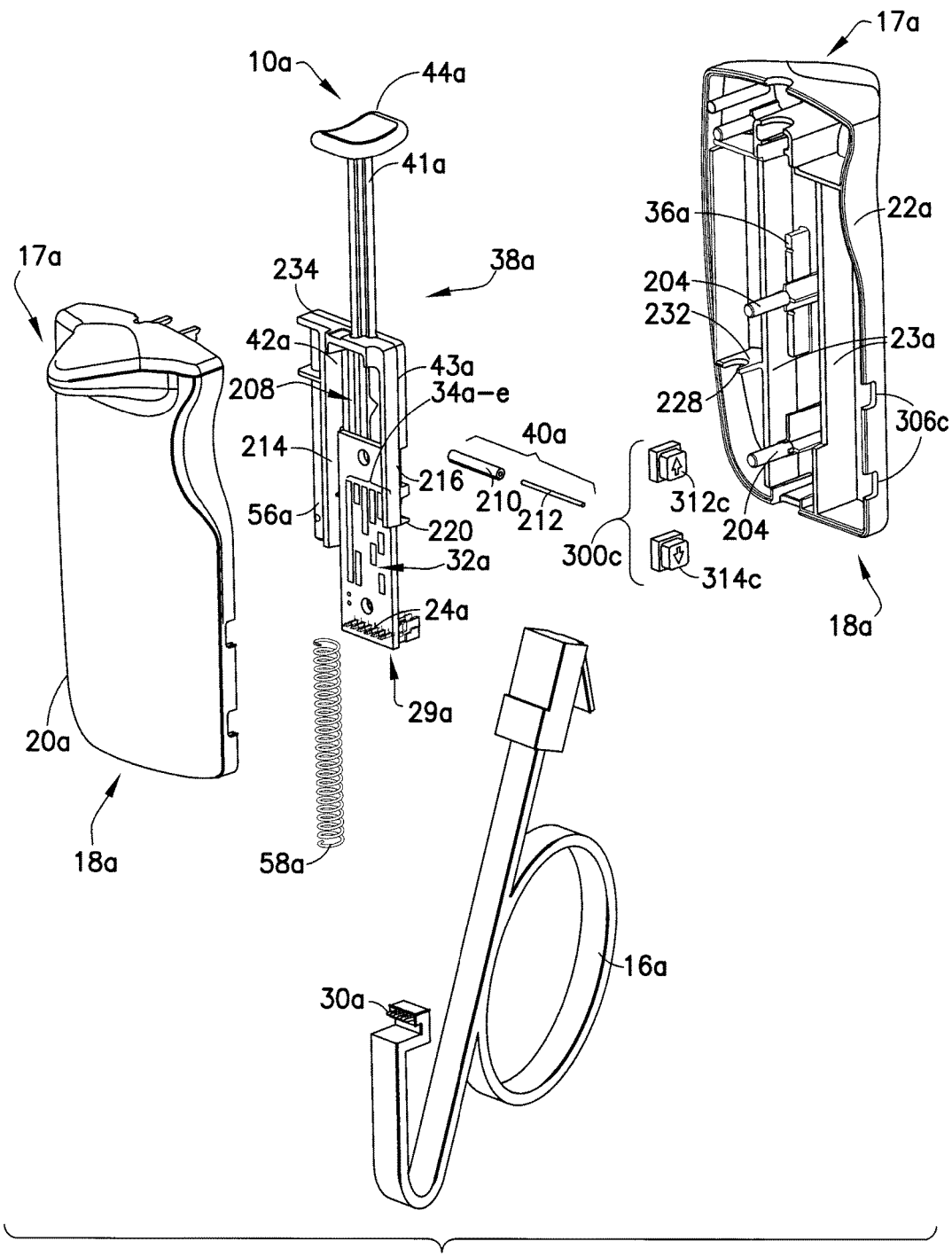
FIG. 12C is an exploded perspective view of the mixing control device of FIGS. 12A-12B.

FIGS. 12A-12C illustrate a third modification 300*c* to control device 10*a* wherein the ratio of contrast to saline is controlled by a pair of push buttons 312*c*, 314*c* electrically connected to electronic substrate 24*a*. As is well-known in the electronics field, electrical push buttons are used to produce electrical inputs to electronic substrates. In the present embodiment, an "up" push button 312*c* and a "down" push button 314*c* are provided to interface with electronic substrate 24*a* so that pressing either button (repeatedly or continuously) produces a range of output signals from the electronic substrate 24*a* that is outputted via cable 16*a* to control unit(s) of the fluid delivery system 100 and instructs the same to operate, for example, in a contrast delivery mode, a saline delivery mode, and a "mixing" mode comprising contrast-saline mixture ratios defined by the "up" and "down" inputs to push buttons 312*c*, 314*c*. Once again, such output signals may be continuously variable and interpreted continuously by the control unit(s) of the fluid delivery system 100 and result in continuously variable changes in the contrast-saline mixture ratios defined by the by the "up" and "down" inputs to push buttons 312*c*, 314*c*. Alternatively, such output signals may be discretely interpreted by the control unit(s) of the fluid delivery system 100 in that discrete (or continuous depressing) of the "up" and "down" push buttons 312*c*, 314*c* provides inputs to the electronic substrate 24*a* which will yield output signals that result in specified or predefined ratios of contrast to saline mixtures to be outputted from the fluid delivery system 100. In this latter operational mode, the fluid delivery system 100 and, more particularly, the control unit(s) of the fluid delivery system 100 interprets the output signals from the electronic substrate 24*a* indicative of the discrete or continuous depressing of the "up" and "down" push buttons 312*c*, 314*c* as specified mixture ratios of contrast to saline. In other words, the control unit(s) may interpret incremental or (or continuous) depressing of push buttons 312*c*, 314*c* as requests for incremental or discrete changes in contrast-saline mixture. The illustrated push buttons 312*c*, 314*c* may extend through respective openings 306*c* in housing 12*a* so as to be accessible by the operator's fingers. Housing portion 22*a* of housing 12*a* may again define internal support structure for supporting push buttons 312*c*, 314*c* in a similar manner to button 66*a* discussed previously.

In exemplary operation, depressing one or the other of push buttons 312*c*, 314*c* results in changes in the mixture ratio of contrast to saline. For example, if the medical practitioner desires more contrast and less saline, he or she may press (either multiple times or with continuous pressure) the "up" push button 312*c* which inputs an electrical signal to the electronic substrate 24*a*. Electronic substrate 24*a* provides output signals to the control unit(s) of the fluid delivery system 100 indicating that additional contrast is desired. Typically, at some preselected point in time or after a preselected number of "pushes", a contrast delivery of 100% contrast media is reached and further depressing of the push button 312c yields no further effect. In other words, depressing push button 312c continuously or possibly repeatedly sends electrical signals to the electronic substrate 24a which provides output signals to the control unit(s) of the fluid delivery system 100 which ultimately determines that the operator desires a 100% contrast event. Depressing (continuously or intermittently) push button 314c thereafter results in output signals from the electronic substrate 24a that saline is now desired. The fluid delivery system 100 responds with an increasing percentage of saline. As noted in the foregoing, the output signals may be continuously monitored and responded to by the fluid delivery system 100 thereby resulting in continuously variable ratios of contrast to saline mixtures. Alternatively, discrete or continuous depressing of the push buttons 312c, 314c may result in discrete ratio changes, such as a 10% incremental change for each depression of the respective push buttons 312c, 314c, as determined by the control unit(s) of the fluid delivery system 100. To further clarify, the control unit(s) of the delivery system 100 may have stored therein a series of predefined resistance values of the push buttons 312c, 314c which correspond to a variety of different contrast saline mixes. Accordingly, as a user intermittently or continuously pushes one of push buttons 312c, 314c, the control unit(s) will only instruct fluid delivery system 100 to change the ratio of contrast to saline when one of the predefined resistance values is met. In this manner, intermittent or continuous depressing of push buttons 312c, 314c can be converted to discrete mixture ratios by the control unit(s). As with the two previously embodiments, tactile indicators (physical and/or audible "clicks" or other sensory alerts associated with push buttons 312c, 314c) may denote each increment change which corresponds to a predetermined mixture ratio.

Figure 13A:
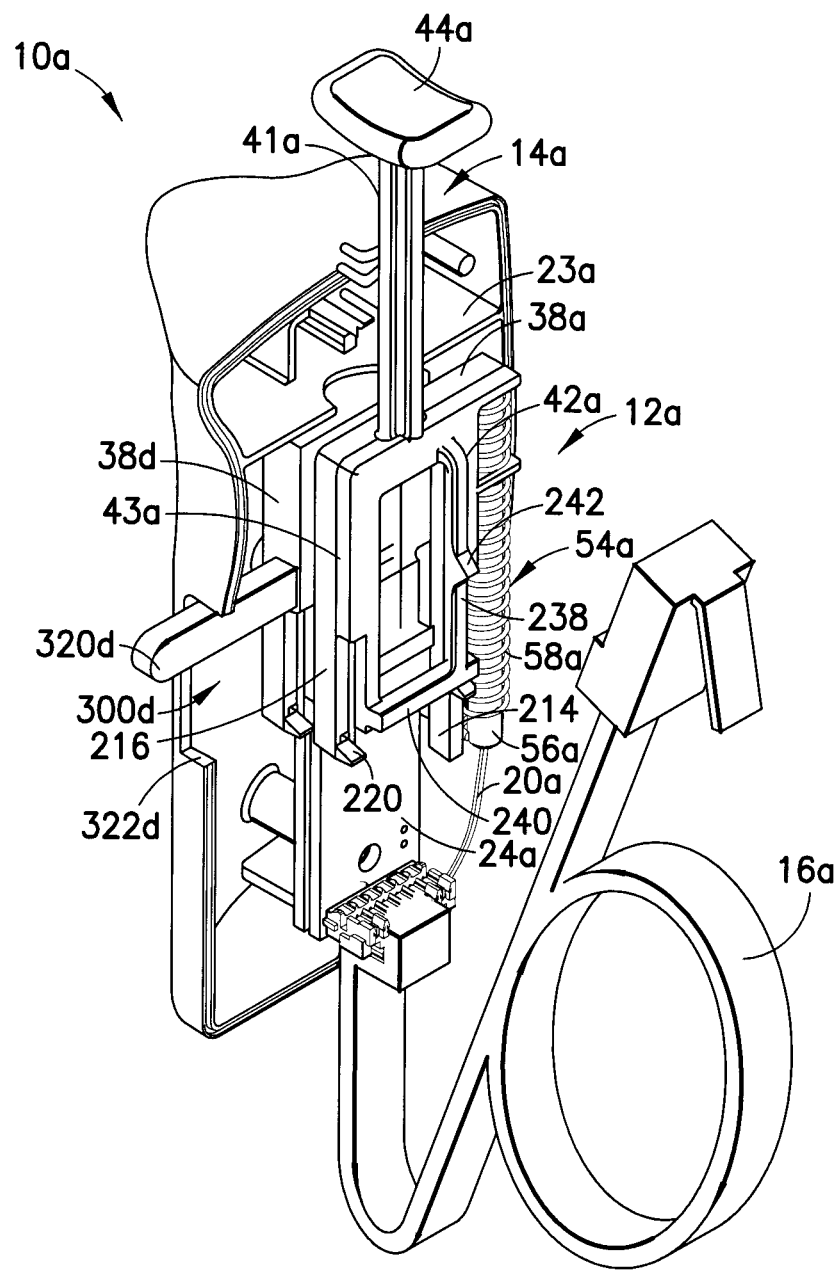
FIG. 13A is a perspective view of a fourth embodiment of a mixing control device and showing right side internal details thereof.
Figure 13B:
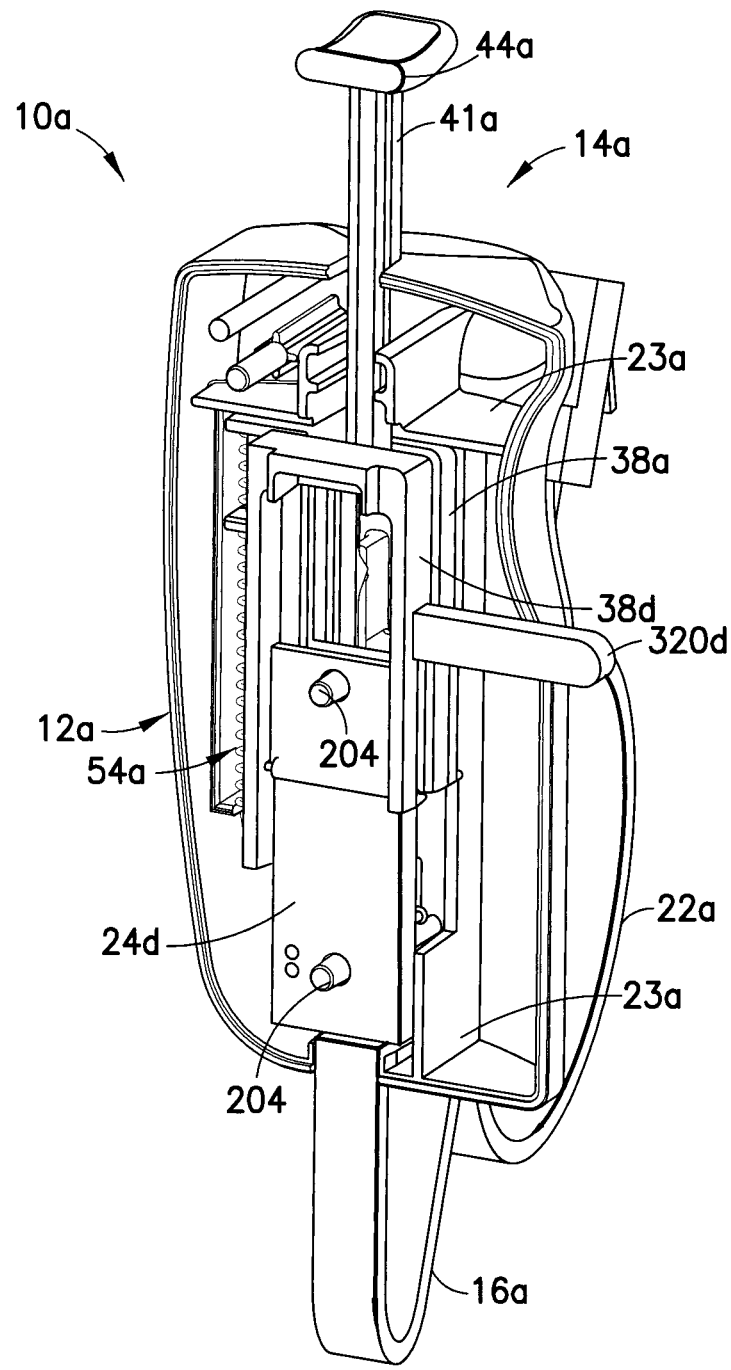
FIG. 13B is a perspective view of the mixing control device of FIG. 13A showing left side internal details thereof.
Figure 13C:
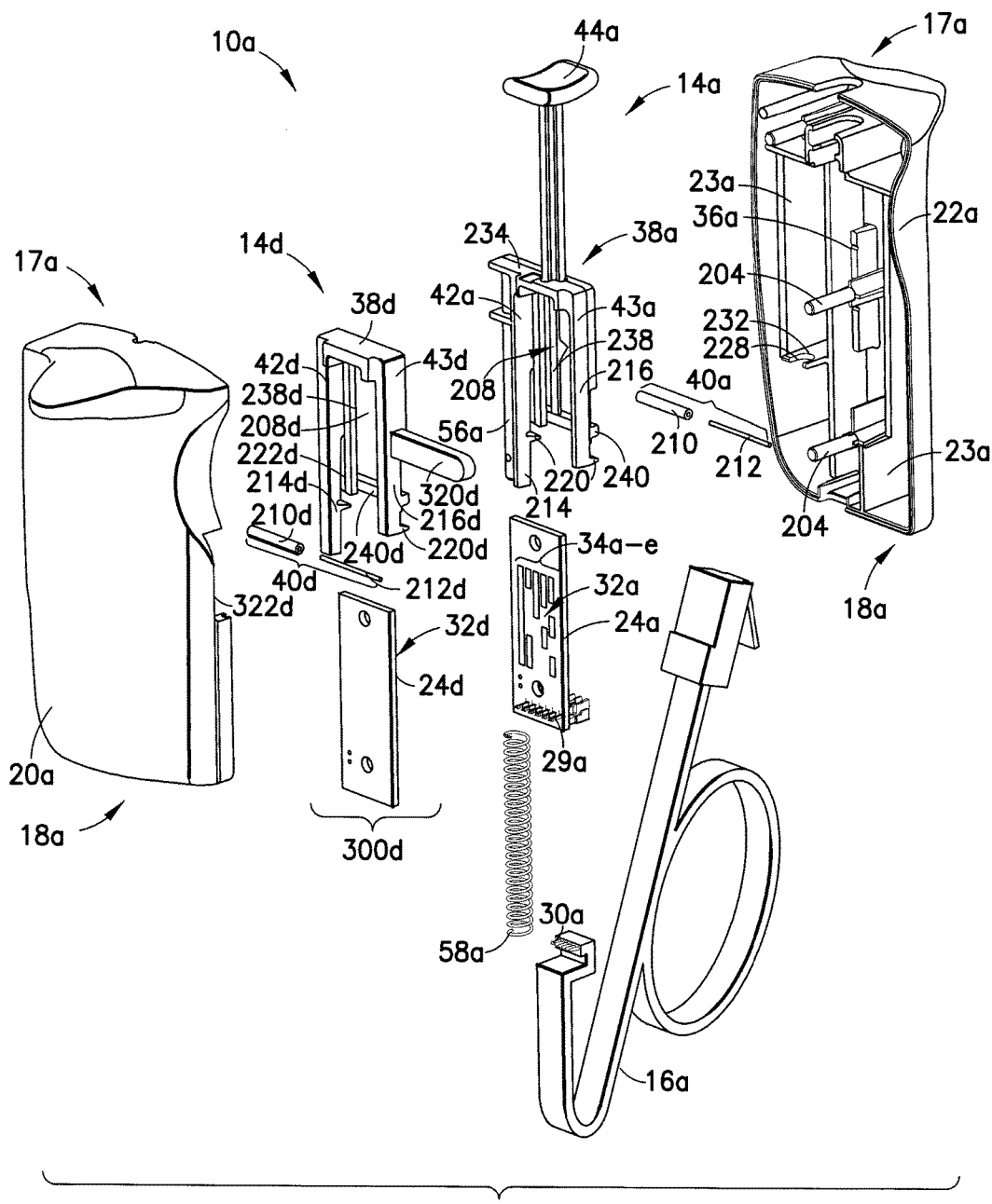
FIG. 13C is an exploded perspective view of the mixing control device of FIGS. 13A-13B.

In one further modification 300d to control device 10a shown in FIGS. 13A-13C, the ratio of contrast to saline is controlled by an electromechanical interacting arrangement similar to the contact roller 40a and electronic substrate 24a discussed previously. In particular, a second electronic substrate 24d is provided opposite from electronic substrate 24a. Additionally, an actuator 14d comprising an actuating structure 38d, which is similar to actuating member 38a, is provided to move relative to electronic substrate 24d. Actuating member 38d includes rails 42d, 43d to receive the electronic substrate 24d therebetween. Electronic substrate 24d is associated with housing portion 20a of housing 12a in a generally similar manner to the way electronic substrate 24a is associated with housing portion 22a of housing 12a discussed previously.

In the present embodiment, the actuating member 38d is configured to support a contact roller 40d similar to contact roller 40a in the manner discussed previously. The contact roller 40d includes roller 210d rotationally mounted on an axle 212d. The axle 212d is in turn rotationally supported by the actuating member 38d. To support the contact roller 40d, the rails 42d, 43d of the actuating member 38d include extended support members 214d, 216d adapted to rotationally support the axle 212d. The support members 214d, 216d define opposing notches or recesses 218d for rotationally supporting the ends of the axle 212d. The support members 214d, 216d further include guide tabs or ramps 220d disposed immediately adjacent the notches 218d to guide entry of the ends of the axle 212d into the notches 218d.

The support members 214d, 216d define longitudinal gaps 222d with distal ends 224d, 226d of the rails 42d, 43d. The longitudinal gaps 222d allow the respective support members 214d, 216d to flex relative to the distal ends 224d, 226d of the rails 42d, 43d when the contact roller 40d is mounted to the support members 214d, 216d and engaged with the electronic substrate 24d. The actuating member 38d includes a handle member 320d extending laterally from rail 43d and through a side opening 322d in housing 12a defined by the opposing housing portions 20a, 22a forming housing 12a. Handle member 320d permits movement of actuating member 38d up and down within the housing 12a in the manner explained in detail previously. In the manner discussed previously, due to the engagement of the roller 210d with the electronic substrate 24d, the support members 214d, 216d will be flexed outward (i.e., generally transversely) a small distance from the rails 42d, 43d and, more particularly, outward from the distal ends 224d, 226d of the rails 42d, 43d. The "flexure" of the support members 214d, 216d is caused by sizing the distance between the root of the notches 218d and the surface of the electronic substrate 24d slightly smaller than the diameter of the roller 210d. This flexure applies a return or "back" pressure on the roller 210d through the axle 212d and causes the resilient material of the roller 210d to deform and "mold" into engagement with conductive pattern 32d on the electronic substrate 24a. Desirably, structure is provided in association with rail 42d which engages, for example frictionally or by intermittent interference engagement, with structure in housing portion 20a such that handle or actuating member 320d may have physically discrete incremental positions within the side opening 322d which correspond, for example, with discrete fluid mixture ratios to be delivered by the fluid delivery system 100 as described further herein.

In view of the foregoing disclosure, it should be clear that electronic substrate 24d comprises a conductive pattern 32d in the form of discrete digital values much like that described in connection with electronic substrate 24a but now these discrete digital values define discrete mixture ratios of contrast and saline to be delivered by the fluid delivery system 100. Accordingly, the engagement of the contact roller 40d with the conductive pattern 32d provides a range of discrete output signals to the control unit(s) of the fluid delivery system 100 which is interpreted by the fluid delivery system 100 as discrete mixture ratios of contrast and saline (or any two desired fluid) to be delivered to a patient. Typically, the digital values forming the conductive pattern 32d may be arranged such that the discrete mixture ratios are linearly proportional to distance of movement of the actuating member 38d. This distance of movement may correspond to the handle member 320d being initially at the top end of the side opening 322d in housing 12a and being moved to the bottom end of side opening 322d or vice versa. As with electronic substrate 24a, the digital values forming conductive pattern 32d may have any desired incremental increase between digital values. For example, each incremental digital value may define a 5%, 10%, 20%, etc. increase and this corresponds to similar discrete increases (5%, 10%, 20%, etc.) in mixture ratios of contrast and saline delivered by the fluid delivery system 100.

As an example, for the purposes of explanation, it may be assumed that with the handle member 320d in a fully "up" position in side opening 322d, a 100% saline delivery will be initiated upon depressing actuator 14a on control device 10a. As the operator pushes downward on handle member 320d, the contact roller 40d moves downward along conductive pattern 32d on electronic substrate 24d and sequentially engages the digital values forming the conductive pattern 32d. If it is assumed that the conductive pattern 32d is formed by eleven digital values then each sequential digital value engaged by the contact roller 40*d* as a result of downward movement of the handle member 320*d* will increase the percentage of contrast being delivered by 10%. As suggested previously, physical structure on rail 42*d* of actuating member 38*d* may engage corresponding structure in housing portion 12*a* to physically and tactilely indicate each incremental position of the handle member 320*d* and, thereby, each incremental increase in contrast percentage delivery in the present example. As the handle member 320*d* reaches the bottom end in side opening 322*d*, a last incremental position is reached and this corresponds to a 100% contrast delivery in the present example. At this last position, depressing the actuator 14*a* on control device 10*a* will cause 100% contrast to be delivered and the further the actuator 14*a* is depressed the greater the flow rate delivered by the fluid delivery system 100.

In each of the foregoing mixing modifications 300*a*-300*d*, it will be clear that the actuator 14*a* is used to control the overall flow rate from the fluid delivery system 100 whereas each of the various modifications 300*a*-300*d* determines the fluid mixture ratio of contrast to saline. In the fluid delivery system 100, powered injector 102 is used to provide the motive forces to inject contrast media into a patient and a pump device is provided on fluid control module 106 to provide the motive force to inject saline into the patient. With the foregoing mixing modifications 300*a*-300*d*, it will be clear that actuation of actuator 14*a* results in discrete changes in overall flow rate from the fluid delivery system 100, whether the fluid being delivered is contrast-only, saline-only, or a mixture of these fluids. Actuation of the various devices forming mixing modifications 300*a*-300*d* is intended to instruct the fluid delivery system 100 as to the desired mixture ratio. This latter actuation may cause the injector 102 and/or pump device on the fluid control module 106 to alter the speed of delivery of contrast and saline in order to meet the desired mixture ratio and the control unit(s) of the fluid delivery system 100, whether residing in the injector 102 and/or fluid control module 106 is capable of responding to both a desired flow rate request (which results from actuation of actuator 14*a*) and a desired mixture ratio request (which results from actuation of actuator 14*d*). The programming in the control unit(s) of the fluid delivery system 100 is capable of responding to requests for increased or decreased flow rate and increased or decreased mixture ratios as desired by the user.

Figure 14:
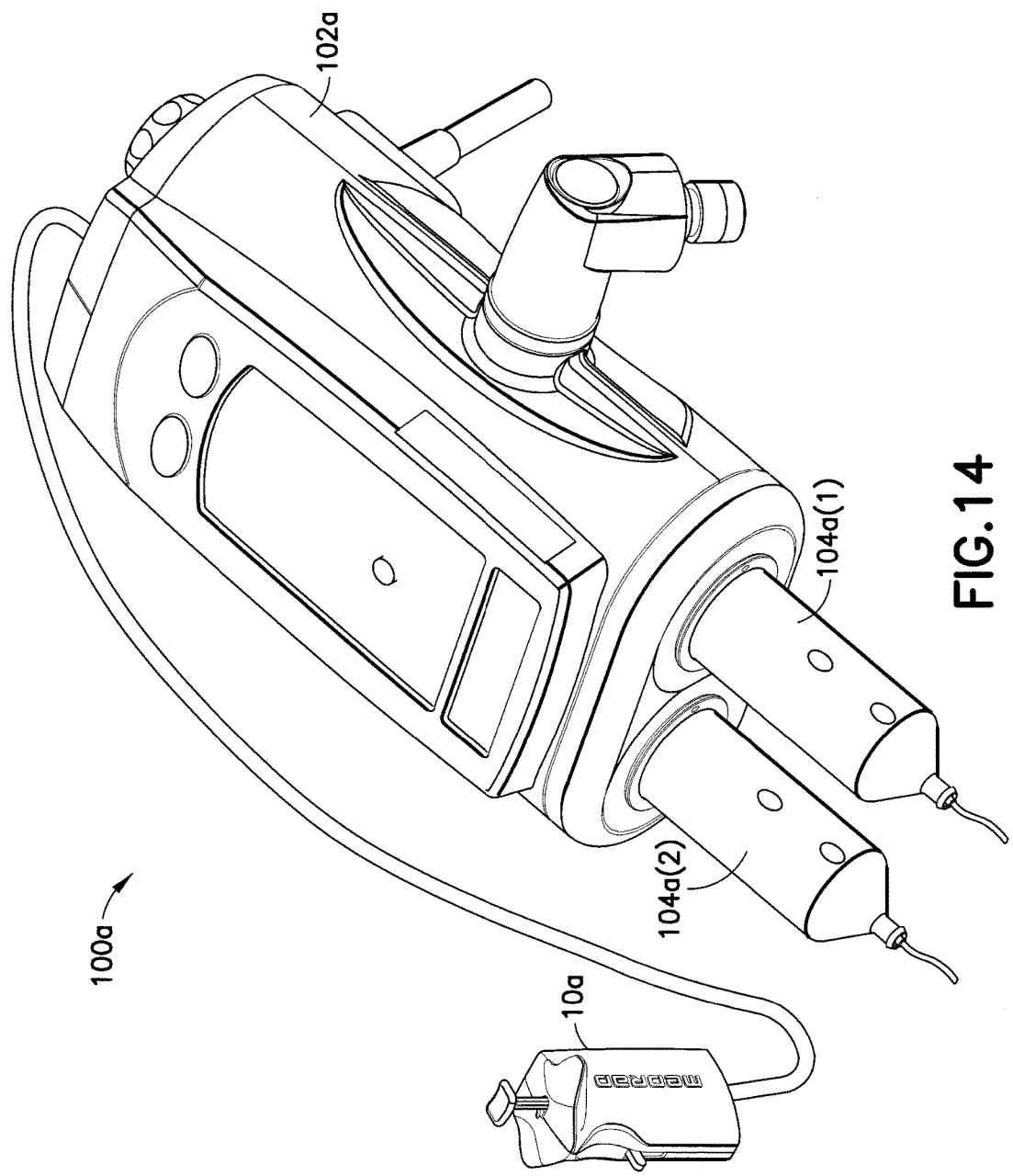
FIG. 14 is a perspective view of a fluid delivery system incorporating multiple syringes and which illustrates use of a mixing control device as found in FIGS. 10-13.

FIG. 14 illustrates an alternative embodiment of fluid delivery system 100*a* comprising a powered injector 102*a* adapted to interface with two syringes 104*a*(1), 104*a*(2) which may be fluidly connected to a source of contrast media (not shown) and a source of saline (not shown) or any two desired fluids. Mixing control device 10*a* may be interfaced with injector 102*a* in a similar manner to that described previously in connection with fluid delivery system 100 described previously and provides inputs to the control unit, for example, housed in injector 102*a* so the control inputs to the mixing control device 10*a* causes the injector 102*a* to provide desired flow rates and desired contrast-saline mixtures based on the user's inputs to control device 10*a*. A suitable multi-syringe injector for powered injector 102*a* is described in U.S. patent application Ser. No. 09/765,498, filed on Jan. 18, 2001, and now U.S. Pat. No. 7,018,363 assigned to the assignee of the present application, the disclosure of which is incorporated herein by reference in its entirety. Other relevant multi-fluid delivery systems are found in U.S. patent application Ser. No. 10/159,592, filed on May 30, 2002 (published as U.S. 2004/0064041) and in U.S. patent application Ser. No. 10/722,370, filed Nov. 25, 2003 (published as U.S. 2005/0113754), assigned to the assignee of the present application, and the disclosures of which are both incorporated herein by reference.

While the present disclosure was described with reference to exemplary and alternative embodiments, those skilled in the art may make modifications and alterations without departing from the scope and spirit of the disclosure. Accordingly, the foregoing detailed description is intended to be illustrative rather than restrictive. The disclosure is defined by the appended claims, and all changes to the disclosure that fall within the meaning and range of equivalency of the claims are to be embraced within their scope.

We claim:

1. A fluid delivery system for use in medical procedures to deliver multiple injection fluids to a patient, the fluid delivery system comprising:
   an injector for delivering a first of the multiple injection fluids to the patient;
   a fluid control device for delivering a second of the multiple injection fluids to the patient; and
   a manual control device operatively associated with the injector and the fluid control device, the manual control device comprising:
      a first actuator associated with the manual control device, wherein the first actuator controls discrete mixture ratios of the first and the second of the multiple injection fluids to the patient; and
      a second actuator associated with the manual control device, wherein the second actuator controls a flow rate of the first and the second of the multiple injection fluids to the patient,
   wherein actuation of the first actuator initiates first output signals to a control unit to deliver the first and the second of the multiple injection fluids in one of the discrete mixture ratios of the first and the second of the multiple injection fluids to the patient,
   wherein actuation of the second actuator initiates a second output signal to the control unit to control the flow rate of the first and the second of the multiple injection fluids to the patient.

2. The fluid delivery system of claim 1, further comprising an electronic substrate disposed within the manual control device,
   wherein the second actuator is adapted to operatively associate with the electronic substrate when actuated by a user, and wherein the electronic substrate comprises a plurality of predetermined digital values corresponding to a selected flow rate of a selected ratio of one or more of the discrete mixture ratios of the first and second of the multiple injection fluids to be delivered to the patient, such that when the second actuator is actuated, the second actuator operatively associates with the electronic substrate and transmits one or more of the plurality of predetermined digital values to the control unit.

3. The fluid delivery system of claim 2, wherein the second actuator is movably associated with the manual control device and the plurality of predetermined digital values are arranged such that the selected flow rate increases in linear proportion to a distance the second actuator is moved.

4. The fluid delivery system of claim 2, wherein the second actuator is movably associated with the manual control device and the plurality of predetermined digital values are arranged such that the selected flow rate incrementally increases with a distance the second actuator is moved.

5. The fluid delivery system of claim 4, wherein the plurality of predetermined digital values comprise at least a first digital value corresponding to no movement of the second actuator and no flow rate from the fluid delivery system, and a last digital value corresponding to a maximum movement of the second actuator and a maximum flow rate from the fluid delivery system.

6. The fluid delivery system of claim 2, wherein the second actuator is movably associated with the manual control device and comprises an actuating member and a contact roller adapted to operatively associate with a conductive pattern on the electronic substrate.

7. The fluid delivery system of claim 1, wherein the first actuator comprises a potentiometer.

8. The fluid delivery system of claim 7, wherein the potentiometer is one of a linear potentiometer and a rotational potentiometer.

9. The fluid delivery system of claim 1, wherein the first actuator comprises at least one push button.

10. The fluid delivery system of claim 1, wherein the manual control device is operatively associated with the injector and the fluid control device by a wired cable.

11. A manual control device for controlling a multi-fluid delivery system delivering at least a first injection fluid and a second injection fluid to a patient, the manual control device comprising:
    a first actuator associated with the manual control device, wherein the first actuator controls discrete mixture ratios of the at least the first injection fluid and the second injection fluid; and
    a second actuator associated with the manual control device, wherein the second actuator controls a flow rate of the at least the first injection fluid and the second injection fluid delivered by the multi-fluid delivery system;
    wherein actuation of the first actuator initiates first output signals to a control unit of the multi-fluid delivery system to deliver the at least the first injection fluid and the second injection fluid in one of the discrete mixture ratios of the at least the first injection fluid and the second injection fluid, and
    wherein actuation of the second actuator initiates a second output signal to the control unit to control the flow rate of the at least the first injection fluid and the second injection fluid.

12. The control device of claim 11, further comprising an electronic substrate disposed within the manual control device,
    wherein the second actuator is adapted to operatively associate with the electronic substrate when actuated by a user, and
    wherein the electronic substrate comprises a plurality of predetermined digital values corresponding to a selected flow rate of the at least the first injection fluid and the second injection fluid to be delivered to the patient such that when the second actuator is actuated, the second actuator operatively associates with the electronic substrate and transmits one or more of the plurality of predetermined digital values to the control unit.

13. The control device of claim 12, wherein the second actuator is movably associated with the manual control device and the plurality of predetermined digital values are arranged such that the selected flow rate of the at least the first injection fluid and the second injection fluid increases in linear proportion to a distance the second actuator is moved.

14. The control device of claim 12, wherein the second actuator is movably associated with the manual control device and the plurality of predetermined digital values are arranged such that the selected flow rate of the at least the first injection and the second injection fluid incrementally increases with a distance the second actuator is moved.

15. The control device of claim 14, wherein the plurality of predetermined digital values comprise at least a first digital value corresponding to no movement of the second actuator and no flow rate from the multi-fluid delivery system, and a last digital value corresponding to a maximum movement of the second actuator and a maximum flow rate from the mufti-fluid delivery system.

16. The control device of claim 12, wherein the second actuator is movably associated with the manual control device and comprises an actuating member and a contact roller adapted to operatively associate with a conductive pattern on the electronic substrate.

17. The control device of claim 11, wherein the first actuator comprises a potentiometer.

18. The control device of claim 17, wherein the potentiometer is one of a linear potentiometer and a rotational potentiometer.

19. The control device of claim 11, wherein the first actuator comprises at least one push button.

20. The control device of claim 11, wherein the manual control device is operatively associated with the multi-fluid delivery system by a wired cable.

* * * * *

UNITED STATES PATENT AND TRADEMARK OFFICE
CERTIFICATE OF CORRECTION

PATENT NO. : 10,441,716 B2
APPLICATION NO. : 15/864448
DATED : October 15, 2019
INVENTOR(S) : Schriver et al.

Page 1 of 1

It is certified that error appears in the above-identified patent and that said Letters Patent is hereby corrected as shown below:

In the Claims
In Column 32, Line 25, in Claim 14, delete "and" and insert -- fluid and --, therefor.
In Column 32, Line 33, in Claim 15, delete "mufti-fluid" and insert -- multi-fluid --, therefor.

Signed and Sealed this
Fourteenth Day of January, 2020

Andrei Iancu
*Director of the United States Patent and Trademark Office*